(12) United States Patent
Bai et al.

(10) Patent No.: US 11,988,734 B2
(45) Date of Patent: May 21, 2024

(54) METHOD AND APPLICATION FOR MEASURING THE INTRACELLULAR WATER TRANSMEMBRANE EFFLUX RATE, AND MEASUREMENT METHOD AND SYSTEM FOR MAGNETIC RESONANCE IMAGING BIOMARKER OF GLIOMA

(71) Applicant: ZHEJIANG UNIVERSITY, Hangzhou (CN)

(72) Inventors: Ruiliang Bai, Hangzhou (CN);
Yinhang Jia, Hangzhou (CN);
Yingchao Liu, Hangzhou (CN);
Guangxu Han, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 18/039,709

(22) PCT Filed: Jun. 16, 2022

(86) PCT No.: PCT/CN2022/099102
§ 371 (c)(1),
(2) Date: May 31, 2023

(87) PCT Pub. No.: WO2023/134116
PCT Pub. Date: Jul. 20, 2023

(65) Prior Publication Data
US 2023/0349997 A1   Nov. 2, 2023

(30) Foreign Application Priority Data

Jan. 13, 2022  (CN) .......................... 202210037257.9
Jun. 13, 2022  (CN) .......................... 202210666908.0

(51) Int. Cl.
*G01R 33/563*  (2006.01)
*G01R 33/56*   (2006.01)

(52) U.S. Cl.
CPC ... *G01R 33/56308* (2013.01); *G01R 33/5601* (2013.01)

(58) Field of Classification Search
CPC .............. G01R 33/465; G01R 33/5601; G01R 33/5608; G01R 33/56308; G01R 33/5633;
(Continued)

(56) References Cited

U.S. PATENT DOCUMENTS

2004/0242994 A1   12/2004  Brady et al.
2015/0141804 A1*   5/2015  Rooney ............... A61B 5/0263
                                              600/419
(Continued)

FOREIGN PATENT DOCUMENTS

| CN | 110226098   | 9/2019  |
| CN | 110391016   | 10/2019 |
| WO | WO2019241266 | 12/2019 |

*Primary Examiner* — Steven L Yeninas
(74) *Attorney, Agent, or Firm* — Jiwen Chen; Joywin IP Law PLLC

(57) ABSTRACT

The invention discloses a method for measuring the intracellular water transmembrane efflux rate ($k_{io}$): setting magnetic resonance imaging parameters and measuring the noise level during scanning. Optimizing the flip angle and resetting it through Monte Carlo simulation. Scanning quantitative T1 imaging. Scanning dynamic-contrast-enhanced magnetic resonance imaging and injecting contrast agent. The full shutter speed model ($SSM_{full}$) is used to analyze every voxel in the tumor area and obtain the $k_{io}$ of them. This method significantly improves the accuracy of $k_{io}$. The invention discloses the measuring method, system and application of $k_{io}$ as a magnetic resonance imaging biomarker of glioma, which is not for disease diagnosis, to evaluate the expression level of AQP4. The invention discloses the application of $k_{io}$ as a magnetic resonance imaging marker of glioma in the preparation of a product for predicting the sensitivity of glioma radiotherapy and chemotherapy.

(Continued)

Through the above methods, systems and applications, the non-invasive and quantitative measurement and imaging of AQP4 expression level in glioma have been realized.

12 Claims, 15 Drawing Sheets

(58) Field of Classification Search
CPC ... G01R 33/56341; A61B 5/0042; A61B 5/05; A61B 5/055; A61B 6/481; A61B 6/501601
See application file for complete search history.

(56) References Cited

U.S. PATENT DOCUMENTS

| | | |
|---|---|---|
| 2018/0275235 A1 | 9/2018 | Reeder et al. |
| 2020/0333417 A1 | 10/2020 | Svedin et al. |
| 2021/0304899 A1* | 9/2021 | Springer .......... G01R 33/56341 |

* cited by examiner

METHOD AND APPLICATION FOR MEASURING THE INTRACELLULAR WATER TRANSMEMBRANE EFFLUX RATE, AND MEASUREMENT METHOD AND SYSTEM FOR MAGNETIC RESONANCE IMAGING BIOMARKER OF GLIOMA

This is a U.S. national stage application of PCT Application No. PCT/CN2022/099102 under 35 U.S.C. 371, filed Jun. 16, 2022 in Chinese, claiming priority of Chinese Application No. 202210666908.0, filed Jun. 13, 2022 and Chinese Application No. 202210037257.9, filed Jan. 13, 2022, all of which are hereby incorporated by reference.

TECHNICAL FIELD

The present invention belongs to technical field of magnetic resonance imaging, in particular to method and application for measuring the intracellular water transmembrane efflux rate, and measurement method and system for magnetic resonance imaging biomarker of glioma.

DESCRIPTION OF RELATED ART

Gliomas are the most prevalent primary central nervous system (CNS) malignancy in adults, comprising approximately 60%-70% of all primary brain tumors. Recently, a large number of studies have shown that the aquaporin channel 4 (AQP4) has important effects to the glioma cells migration, proliferation, and peritumoral edema, and it is an important biomarker for the prognosis of glioma. Compared with normal brain astrocyte, AQP4 increases significantly in glioma, and its expression position is distributed from the endfeet of the astrocyte (around the blood vessels) to the entire cell membrane. Studies have shown that different types of glioma cells AQP4 expression have different reactions to anti-cancer drug temozolomide (TMZ). In summary, AQP4 expression level and position change are one of the early indicators of glioma transformation and treatment resistance.

At present, traditional biopsy is the only standard method to measure the AQP4 expression in vivo. However, the biopsy can only be sampled single or limited point, so that it cannot obtain the spatial distribution and dynamic information of AQP4 in glioma, and it is an invasive method with certain risk. Because gliomas have very strong heterogeneity, partial sampling may come with misjudgment information. Considering the decisive role of AQP4 expression level and spatial heterogenous distribution of AQP4 in the glioma, it is necessary to develop a quantitative imaging technology with high spatial resolution in the body non-invasively. For example, a Chinese patent with the public number CN106683081A proposes a method and system for non-invasive prediction of IDH1 molecular markers for glioma based on radiomics.

In addition, a genetic image-based tumor imaging marker extraction method proposed by a Chinese patent with the public number CN107169497B. CN107169497B uses genetic imaging, and combines the advantages of imaging and molecular technology to invent a non-invasive and interpretable biomarker extraction method. This method extracts the high-dimensional quantitative imaging features of tumor CT and correlates them with corresponding tumor gene expression patterns, and assumes that certain quantitative imaging features can reflect the specific gene expression patterns of tumors and can be used as prognostic biomarkers of tumors. The ultimate goal is to extract non-invasive, biologically interpretable imaging biomarker.

However, AQP4 is still invisible to in vivo imaging methods. It has a relatively low molar concentration (≤[8.65±0.80] ng/ml) in the brain and cannot be detected using either magnetic resonance spectroscopy (MRS) or chemical exchange saturation transfer (CEST). In addition, exogenous contrast agents targeting specific molecules can be used for molecular imaging in MRI. However, no such probes have been developed for AQP4 imaging and the associated drug development and approval processes are both lengthy and costly even if such a probe are available.

Among the normal brain astrocytes, AQP4 is the major water channel expressed in normal CNS and mainly distributed in the end-feet (perivascular) of astrocytes. In glioma, AQP4 is up-regulated and redistributes itself from astrocytic end-feet (perivascular) to the entire cell membrane compared with normal brain astrocytes. The abnormalities of AQP4 expression could facilitate glioma infiltrate into the brain and is one of the earliest indicators of glioma transformation. More importantly, AQP4 has also been shown to be a sensitive prognosis biomarker for human glioma migration, progression, edema, and treatment resistance, and a potential treatment target.

SUMMARY OF THE INVENTION

The object of the present invention is to provide a method of measuring the intracellular water transmembrane efflux rate $k_{io}$, which significantly increases the accuracy of $k_{io}$ measurement. The present invention also provides the application of $k_{io}$ as glioma magnetic resonance imaging biomarker. The present invention also provides a measurement method and system for magnetic resonance imaging biomarker of glioma, so as to realize the non-invasive, quantitative measurement and imaging of AQP4 expression level in glioma. What's more, the present invention also provides an application of $k_{io}$ in preparing products to predict the sensitivity of glioma to chemoradiotherapy, which is beneficial in predicting therapeutic response and promoting precise therapy.

The present invention adopts the following technical scheme:

A method for measuring the intracellular water transmembrane efflux rate $k_{io}$, and this method comprises:
 (1) setting dynamic-contrast-enhanced magnetic resonance imaging (DCE-MRI) scanning parameters, and measuring a noise level of obtained DCE-MRI data.
 (2) optimizing DCE-MRI scanning parameters by using Monte Carlo simulation, and resetting a flip angle of DCE-MRI.
 (3) scanning a quantitative T1 imaging.
 (4) scanning a DCE-MRI and injecting the contrast agent.
 (5) analyzing each voxel in the tumor region by using the Full Shutter-Speed model ($SSM_{full}$), and obtaining the intracellular water transmembrane efflux rate ($k_{io}$), which is also known as the steady-state water molecule cellular efflux rate constant.

In step (2), one or more measured blood plasma contrast agent concentration $C_p$ are randomly selected, and then the simulated DCE-MRI data at different flip angles is generated by using the parameters of human tissue and scanning parameters. The synthesized DCE-MRI time-series signal S(t) is generated by the $SSM_{full}$, and the white noise, whose noise level is the same as the noise level estimated from human DCE-MRI data, is added to S(t). Then noise-added S(t) are fitted by the nonlinear least sum of square algorithm using the $SSM_{full}$. Repeating the above steps and count the fitted $k_{io}$ for simulated DCE-MRI data at each flip angles. Finally, the flip angle with the $k_{io}$ fitting result is closest to the simulated preset value and has the smallest variance is selected as the optimal flip angle. Preferably, repeating more than 100 times. For more specific, full shutter speed model $SSM_{full}$ could refer to CN201910621579.6.

In step (2), the full shutter speed model $SSM_{full}$, divides the water molecules into three compartments: vascular (b), interstitium (o), and intracellular space (i), as well as two water exchange processes, including water exchange between blood and interstitium and water exchange between interstitium and cell. Water exchange in blood and intracellular spaces is negligible. Gd-based contrast agent (CA) (Gd-DTPA, Gadopentetate dimeglumine, (MAGNEVIST) in the present invention is considered an extracellular reagent, distributed only in blood vessels and interstitium. The contrast agent concentration in the interstitial space $[CA_o]$ (T) conforms to the Kety-Schmidt type rate law:

$$[CA_o]<T>=K^{trans}v_0^{-1}\int_0^T[CA_p](t)\exp(-K^{trans}v_0^{-1}(T-t)\,dt,$$

where $v_o$ is the volume fraction of the interstitial space, [CAP] is the concentration of CA in plasma, T is the time period, and t is the time of progression. The full shutter speed model $SSM_{full}$ consists of 5 independents but physiologically relevant parameters: $p_b$-vascular water molar fraction, $p_o$—interstitial water molar fraction, $k_{bo}$—steady-state water molecule extravasation rate constant, $k_{io}$—the steady-state water molecule cellular efflux rate constant, $K^{trans}$—multiplied by the effusion rate constant of CA $K_{pe}$ and plasma volume fraction $v_p(K^{trans}=K_{pc}*v_p=K_{ep}*v_o)$. The intracellular water molar fraction $p_i$ could be yielded from the relationship: $p_o+p_i+p_b=1$.

Preferably, in step (2), the spatial distribution of the actual flip angle should be measured to optimize flip angle in ultra-high field MRI (>3 T). In step (3), the quantitative T1 imaging is measured by multiple flip-angle and short repetition-time sequence.

Preferably, in step (5), using automatic shutter speed analysis method to obtain the vessel contrast agent transfer coefficient ($K^{trans}$) of each voxel in the tumor area. And only the voxels, whose $K^{trans}>0.01$ min$^{-1}$, are further fitted by $SSM_{full}$ model to obtain the intracellular water transmembrane efflux rate ($k_{io}$). For details, please refer to CN201910621579.6.

The above method provided by the present invention is a method for quantitative measurement of $k_{io}$.

The present invention also provides an application of intracellular water transmembrane efflux rate $k_{io}$ as a magnetic resonance imaging biomarker of glioma to evaluate the expression level of AQP4. And the measurement of $k_{io}$ is not limited to the above quantitative method. The application of $k_{io}$ as a magnetic resonance imaging biomarker of glioma can be used for scientific research.

Preferably, the linear relationship between the intracellular water transmembrane efflux rate $k_{io}$ and AQP4 expression level is: cellular AQP4-positive fraction=$(k_{io}-A)/B$, where the range of A is 0.1~0.2 s$^{-1}$ and the range of B is 13.07~15.04 s$^{-1}$.

The present invention also provides a measurement method for evaluating the expression level of AQP4, which is not for disease diagnosis, by using the intracellular water transmembrane efflux rate as the magnetic resonance imaging biomarker of glioma, and the measurement method is:

(1) quantitatively measuring the intracellular water transmembrane efflux rate ($k_{io}$).

(2) using the framed stereotactic biopsy technology to get biopsy tissue and quantitatively measuring its AQP4 expression level.

(3) according to $k_{io}$ and AQP4 expression level, establishing a linear relationship between them.

(4) quantitatively measuring the intracellular water transmembrane efflux rate ($k_{io}$) of the tissue, and the AQP4 expression level of the tissue could be obtained according to the linear relationship in step (3).

Preferably, the measuring method comprises the following steps:

(1) setting dynamic-contrast-enhanced magnetic resonance imaging (DCE-MRI) scanning parameters, and measuring the noise level of obtained DCE-MRI data.

(2) optimizing DCE-MRI scanning parameters by using monte Carlo simulation, and resetting the flip angle of DCE-MRI.

(3) scanning quantitative T1 imaging.

(4) scanning the DCE-MRI and injecting the contrast agent.

(5) analyzing each voxel in the tumor region by using the Full Shutter-Speed model ($SSM_{full}$), and obtaining the intracellular water transmembrane efflux rate ($k_{io}$).

(6) according to the DCE-MRI, use the framed stereotactic biopsy technology to obtain biopsy tissue, and quantitatively measuring its AQP4 expression level.

(7) doing linear regression analysis of $k_{io}$ and AQP4 expression levels, and obtaining the linear equation between AQP4 expression level and $k_{io}$.

(8) repeating steps (3)-(5), convert $k_{io}$ images into AQP4-expression-level imaging according to the linear equation in steps (7) to obtain AQP4-expression-level imaging in tumor.

Preferably, in step (6), the AQP4 immunohistochemical picture of the biopsy tissue is obtained to quantify the AQP4 expression level of the tissue.

Preferably, in step (7), the linear relationship between AQP4 expression level and $k_{io}$ is: cellular AQP4-positive fraction=$(k_{io}-A)/B$, where the range of A is 0.1~0.2 s$^{-1}$ and the range of B is 13.07~15.04 s$^{-1}$.

Preferably, in step (8), AQP4 expression level spatial distribution map can use color coding to improve visibility.

The invention also provides an application of the intracellular water transmembrane efflux rate as a magnetic resonance imaging biomarker of glioma in the preparation of a product for predicting the sensitivity of glioma radiotherapy and chemotherapy.

Here, the drug used in the radiotherapy and chemotherapy treatment is temozolomide.

The present invention also provides a measurement system of glioma magnetic resonance imaging biomarkers, which includes:

image extraction and processing module: quantitatively measuring tissue's intracellular water transmembrane efflux rate ($k_{io}$).

post-processing module: establishing the linear relationship between the $k_{io}$ which is obtained from the image processing module and the AQP4 expression level of the biopsy tissue.

prediction module: obtaining the $k_{io}$ by using the image processing module, and using the linear relationship from post-processing module to predict the AQP4 expression level of tissue.

Preferably, the measuring system comprises:

preprocessing module: setting dynamic-contrast-enhanced magnetic resonance imaging (DCE-MRI) scanning parameters, and measuring the noise level of DCE-MRI data. Through Monte Carlo simulation, optimizing the flip angle of DCE-MRI and resetting the optimized flip angle.

image extraction module: scanning quantitative T1 imaging, scanning DCE-MRI and injecting contrast agent.

image processing module: analyzing each voxel in tumor region by using the Full Shutter-Speed model (SSM-$_{full}$), and obtaining the intracellular water transmembrane efflux rate of each voxel.

post-processing module: establishing the linear relationship between the $k_{io}$ obtained by the image processing module and the AQP4 expression level of biopsy tissue.

prediction module: obtaining the $k_{io}$ by using the image extraction module and image processing module, and using the linear relationship from post-processing module to predict the AQP4 expression level of tissue.

Among them, the repetition time of dynamic enhanced magnetic resonance imaging scanning parameters is kept to the shortest or close to the shortest.

The noise level of dynamic enhanced magnetic resonance imaging can be obtained by scanning normal healthy subjects.

Among them, the present invention optimizes the flip angle in the DCE-MRI acquisition parameters through Monte Carlo simulation to make it most sensitive to the detection of water molecule transmembrane exchange process.

The present invention rapidly injects contrast agent at the eighth frame after scanning. The resonance contrast agent is T1 contrast agent. The dosage is recommended to refer to the instructions of the pharmaceutical manufacturer. 15-20 ml of normal saline is injected immediately after contrast agent injection, and the injection speed is recommended to be 2 ml per second.

Among them, according to dynamic contrast enhanced magnetic resonance imaging, combined with clinical factors, the best biopsy point coordinates were obtained, and then the biopsy tissue was taken stereotactically. Among them, the tumor area can be manually delineated by professional doctors or personnel, or automatically obtained by artificial intelligence. The number of samples of biopsy tissue is 45, which can be further improved to improve the accuracy of $k_{io}$'s characterization of AQP4 level.

In conclusion, compared with the prior technology, the invention has the following technical effects:

1. The present invention is the first time to propose the magnetic resonance imaging biomarker of AQP4 expression in gliomas—the intracellular water transmembrane efflux rate $k_{io}$, and proves that there is a highly linear relationship between AQP4 expression level and $k_{io}$.

2. The present invention provides a dynamic contrast-enhanced magnetic resonance imaging method for quantitatively measuring the intracellular water transmembrane efflux rate $k_{io}$. Through Monte Carlo simulation, the dynamic contrast-enhanced magnetic resonance imaging parameters are optimized, significantly improving the accuracy of this imaging method for $k_{io}$ measurement.

3. The present invention realizes quantitative imaging of AQP4 expression in glioma, and can measure the heterogeneity of AQP4 expression in glioma. The expression level of AQP4 can be used for scientific research, such as the study of the therapeutic effects of some anticancer drugs and new treatment methods, the study of the relationship between the expression level of AQP4 and the pathological processes such as glioma migration and proliferation, and the study of the expression level of AQP4 and the treatment resistance of glioma.

DETAILED DESCRIPTION OF THE INVENTION

In order to make the purpose, technical scheme and advantages of the invention clearer, the technical scheme of the invention will be described clearly and completely in combination with the attached drawings.

Figure 1:
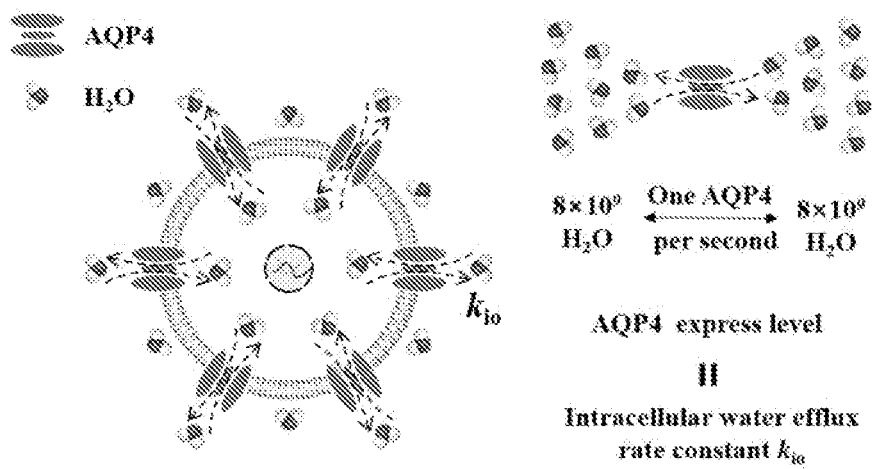
FIG. 1 is the schematic diagram of the magnetic resonance imaging marker of AQP4 designed by the invention: the intracellular water transmembrane efflux rate $k_{io}$ is the magnetic resonance imaging marker of AQP4 expression in glioma.

As shown in FIG. 1, AQP4 signal is represented and amplified by the AQP4-regulated transmembrane water exchange. Studies have shown that one AQP4 molecule is able to transport about 0.24 pL water molecules per second across the membrane (the cell volume of glioma cells is of the order of 10 pL). The intracellular water-efflux rate constant, $k_{io}$, is therefore an ideal and potentially linear surrogate biomarker of membrane AQP4 expression.

Figure 2:
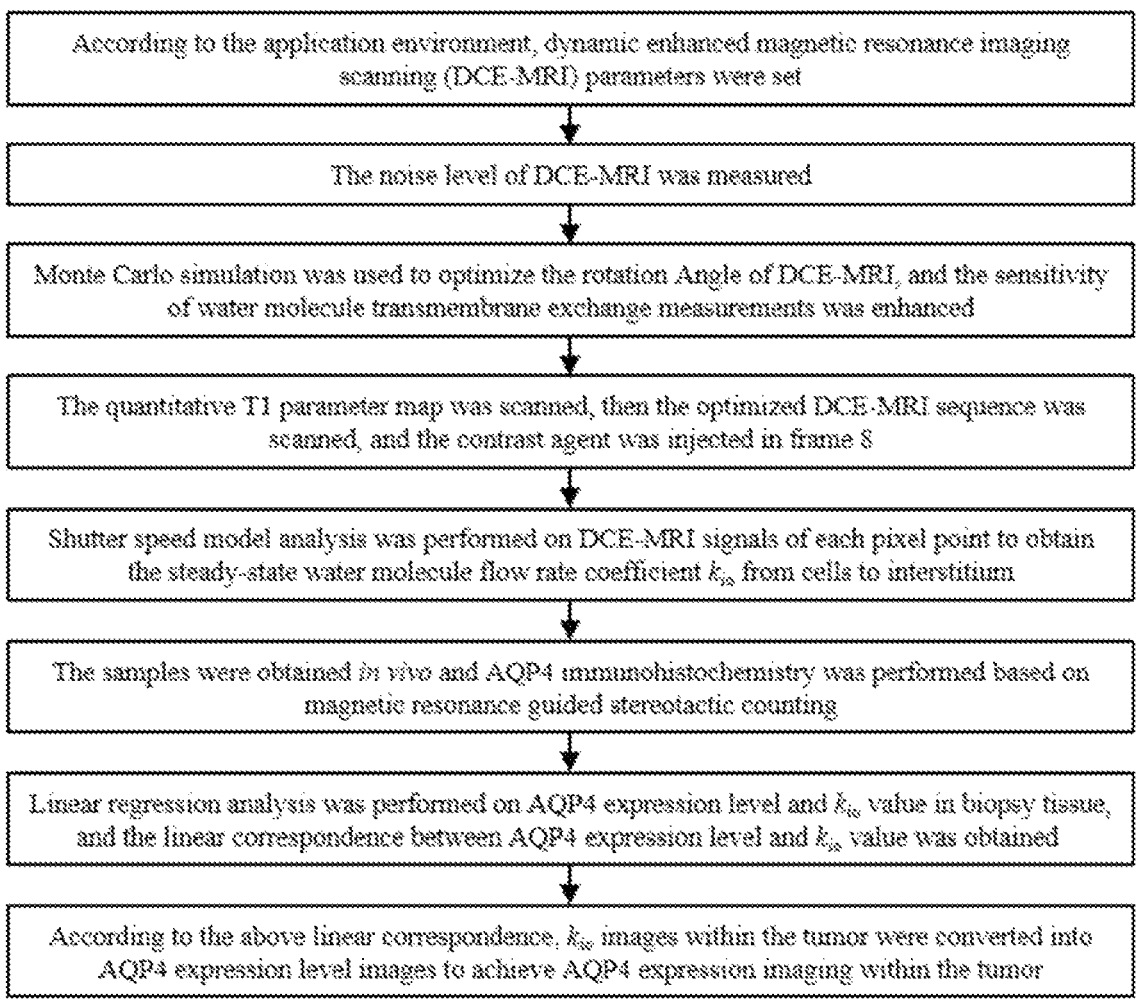
FIG. 2 is the flow chart of the measurement method of magnetic resonance imaging markers of gliomas provided by the invention.

As shown in FIG. 2, the present invention provides a measurement method for magnetic resonance imaging biomarker of glioma comprising:

Step 1: Setting the dynamic contrast enhanced magnetic resonance imaging parameters and measure the noise level during dynamic contrast enhanced magnetic resonance scanning. The specific steps are as follows:
(1) Adjusting the DCE-MRI sequence parameters in the scanner to set the Repetition Time (TR) to the shortest or near the shortest, such as 3 milliseconds.
(2) Adjusting the number of DCE-MRI sequence repeats for 10 min in a normal participant scan to count the noise level.

Figure 3:
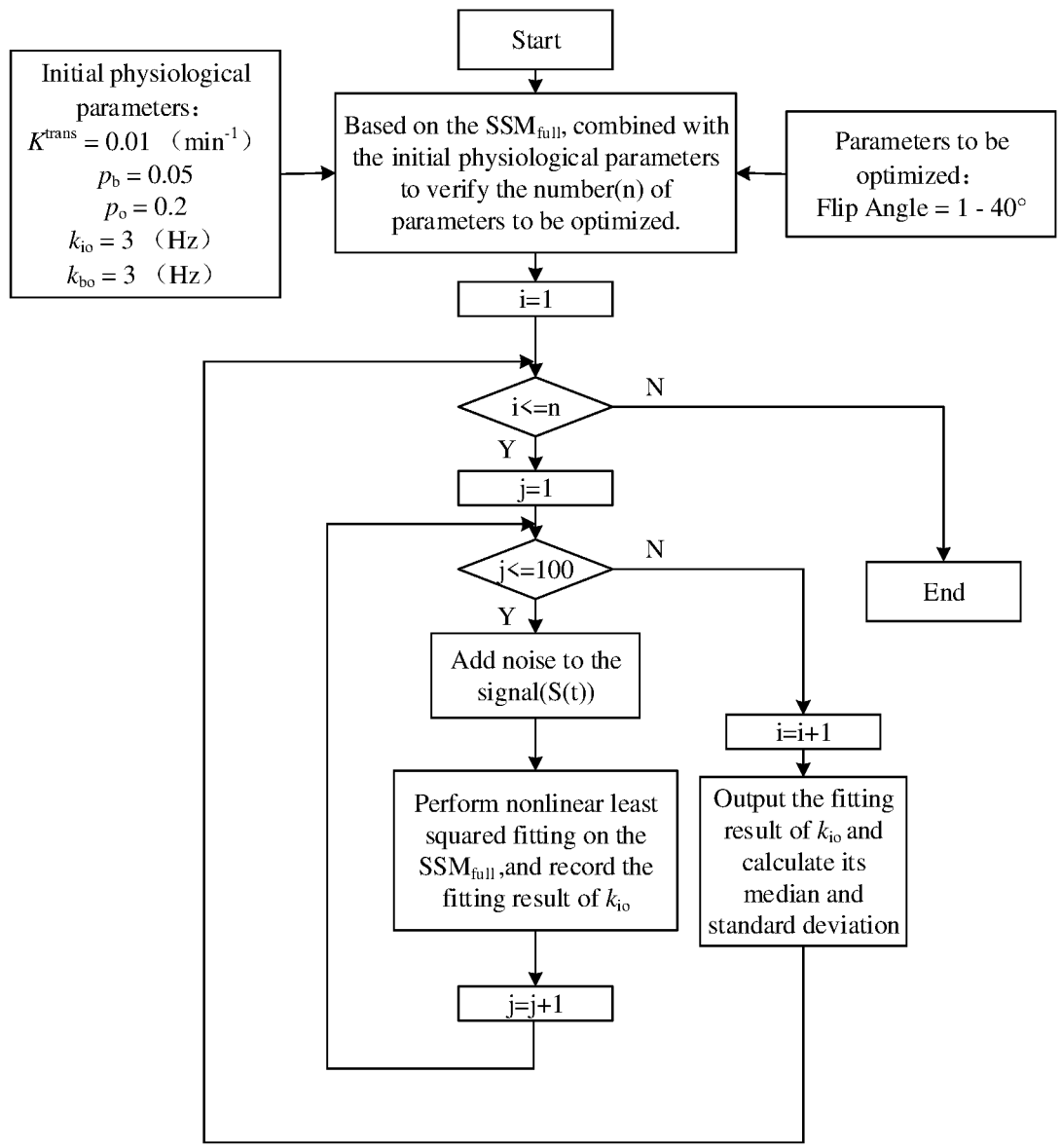
FIG. 3 shows the Monte Carlo simulation flow chart.

Step 2: as shown in FIG. 3, the dynamic contrast enhancement magnetic resonance imaging DCE-MRI acquisition parameters were optimized by Monte Carlo simulation to make it the most sensitive to the detection of water molecules in the transmembrane exchange process.
(1) A set of contrast agent concentration time curves $C_p$ (t) or artificial simulations $C_p$ (t) were selected from the previous dynamic contrast enhanced magnetic resonance imaging data, given the initial physiological parameters: contrast agent exudation rate $K^{trans}$=0.01 (per minute), vascular water molar fraction $p_b$=0.05, interstitial water molar fraction $p_o$=0.2, the steady-state water molecule cellular efflux rate constant $k_{io}$=3 Hz from cell to interstitium, and the steady-state water molecule extravasation rate constant $k_{bo}$=3 Hz.
(2) Setting the parameters to be optimized—the adjustment range of the flip angle is 1-40 degrees.
(3) Setting the simulated dynamic enhanced magnetic resonance parameters to be the same as the actual dynamic enhanced magnetic resonance imaging parameters (except for the flip angle)
(4) DCE-MRI time series signals are generated according to the three-chamber, two-exchange model (the model refers to the full shutter speed model $SSM_{full}$ model mentioned in the patent (patent number ZL 201910621579.6).
(5) Random white noise was applied to the signal, white noise of the same noise level was added according to the noise level estimated by DCE-MRI experiments, and nonlinear least squared fitting was performed on the full shutter speed model $SSM_{full}$ to S(t) based on the method in the patent (patent number ZL 201910621579.6).
(6) Repeating the procedure (3)-(5) 100 times, and count the standard deviation and median of the intracellular water transmembrane efflux rate $k_{io}$ under each replicate.
(7) Repeating the flow (3)-(6) until all sweep parameter combinations are traversed, and the kio fitting result is closest to the simulated preset value and the flip angle whose variance is least is the optimal flip angle.

Figure 4:
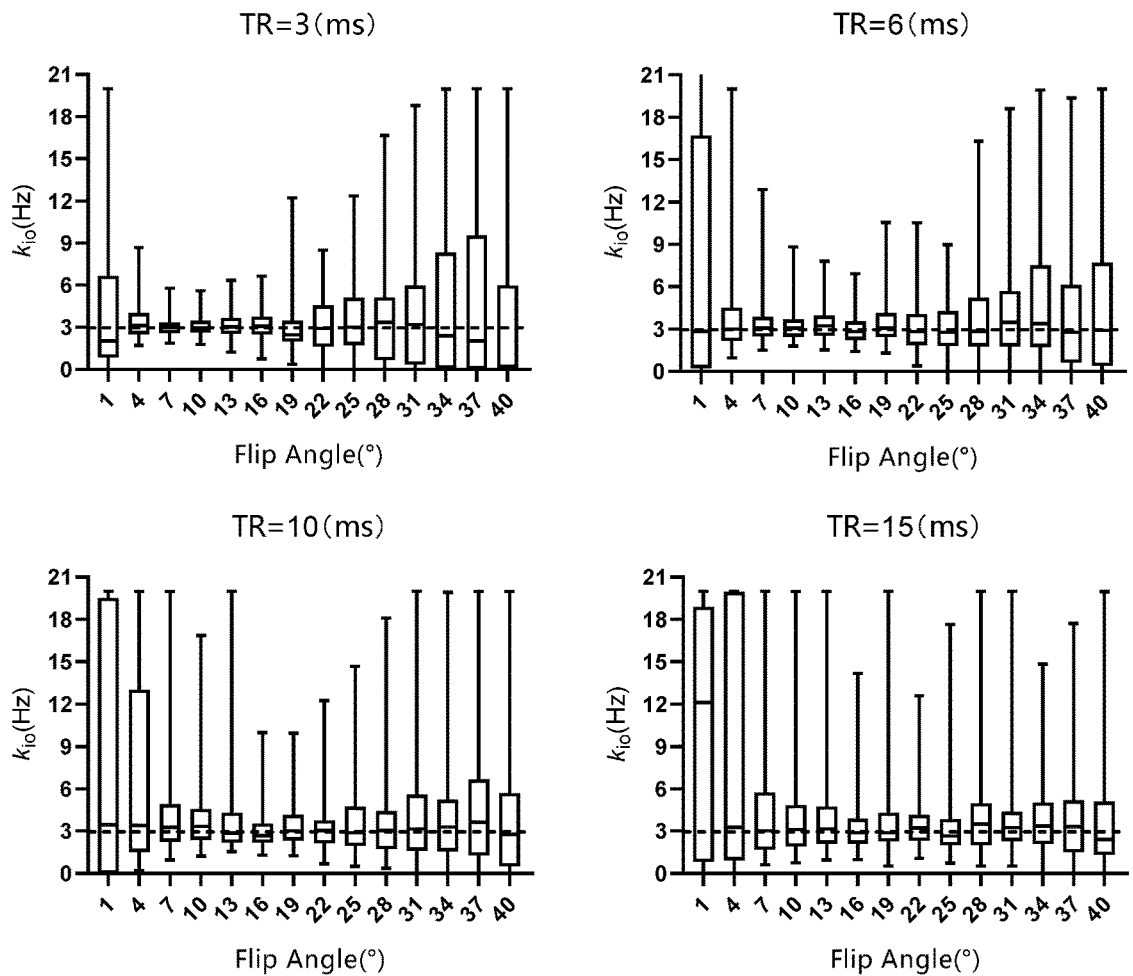
FIG. 4 shows the optimization of the flip angle parameters of dynamic contrast enhanced magnetic resonance imaging by Monte Carlo simulation.

Step 3: according to step 2, selecting the flip angle (as shown in FIG. 4) where the standard deviation of $k_{io}$ is the smallest and the median is closest to the set value, and reset the flip angle of dynamic contrast enhanced magnetic resonance imaging.

Step 4: Scanning quantitative T1 magnetic resonance imaging; The parameters are set as follows:
Field of view (FOV):(340 mm)$^2$; slice thickness: 1.5 mm, 80 slices; voxel size 0.8×0.8×1.5 mm$^3$; Echo time (TE)/TR=2.46 ms/5.93 ms; Flip angle (FA), 2°/14°; Bandwidth, 450 Hz/pixel.

Step 5: Scanning the dynamic enhanced magnetic resonance imaging and bolus injection of contrast agent begins at the eighth frame;
The DCE-MRI data acquired using 3D CAIPIRINHA-Dixon-TWIST were as follows: FOV=340×340×120 mm$^3$; FA=10°; Bandwidth, 1090 Hz/pixel; TR, 6 ms; TE, 1.3 ms; and quickly inject contrast agent in the eighth frame after the start of scanning; Immediately after injection, another 15-20 ml of normal saline is injected, and the injection speed is recommended to be 2 ml per second.

Step 6: using the full shutter speed model $SSM_{full}$, analysis on each voxel in the tumor region is performed, and obtain the intracellular water transmembrane efflux rate $k_{io}$ for each voxel. The detailed steps are as follows:
(1) According to the phenomenon that the enhancement of the contrast agent in the tumor area is higher than that of normal tissue, the tumor area is manually delineated by professional doctors or personnel, or the tumor area is automatically obtained through artificial intelligence methods.
(2) Obtaining dynamic contrast magnetic resonance images DCE-MRI time-series tumor region data in biological individuals blood contrast agent concentration time signal AIF.
(3) According to the blood contrast agent concentration time signal in step (2), the nonlinear minimum sum of squares of the full shutter speed model-$SSM_{full}$ is fitted to the DCE-MRI time series signal of each voxel to obtain the DCE-MRI signal fitting results of each voxel in the tumor area, respectively. After the $SSM_{full}$ is fitted, the distribution map of five physiological parameters is generated, the five physiological parameters include: $K^{trans}$, vascular water molar fraction $p_b$, interstitial water molar fraction $p_o$, steady-state water molecule extravasation rate constant $k_{bo}$ and the steady-state water molecule cellular efflux rate constant $k_{io}$.
(4) The error analysis was performed on the $k_{io}$ and $k_{bo}$ in step (3), leaving the voxel whose the 95% confidence interval in the [0 s$^{-1}$ 20 s$^{-1}$] interval or the lower 95% confidence interval greater than 5 s$^{-1}$, resulting in a distribution map of the final $k_{io}$, $k_{bo}$ and $K^{trans}$ and $p_b$, $p_o$.

Steps 1 to 6 above are a dynamic contrast-enhanced magnetic resonance imaging method for quantitative measurement of $k_{io}$, which can achieve the first inventive object of the present invention: the accuracy of $k_{io}$ is significantly improved.

Step 7: Using the biopsy planning system to obtain the best biopsy point coordinates according to the tumor $k_{io}$ image and clinical factors. The detailed steps are as follows:
(1) 1-2 days before stereotactic biopsy, all patients need carry stereotactic frame on their heads for MRI structural image scanning.
(2) The calculated whole tumor region $k_{io}$ image according to the description in step 6 is registered and fused with the above structural image, and then imported into the stereotactic biopsy planning system for stereotactic biopsy planning.
(3) In the stereotactic biopsy planning system, 3D image reconstruction and surgery simulation are realized by calculating the target coordinates and the trajectory approach angle, and the coordinate entry point and the needle angle of the target in the cerebral cortex region are determined. In each patient, under the most favorable clinical factors, for example, the biopsy track should be designed to avoid entering through the groove, cortical artery, venous structure or ventricle. Multiple ROIs with different $k_{io}$ values were selected.

Step 8: Taking the biopsy tissue stereotactically and obtain the AQP4 immunohistochemical picture of the biopsy tissue to quantify the AQP4 expression level of the tissue:

(1) The tissue samples of all biopsy points were obtained by three neurosurgeons through surgery according to the specified trajectory plan of the biopsy entry point and target point in the stereotactic procedure in step 7. Biopsy is performed under local or general anesthesia. The biopsy needle (inner diameter 2.0 mm, side cutting window 10 mm) is carefully and gently inserted into the target site, and the biopsy tissue samples are obtained clockwise (0°, 90°, 180°, 270°).

(2) A 5-10 mm long specimen was obtained by stereotactic biopsy. Fix and embed the samples that need to undergo immunohistochemistry to obtain AQP4 expression distribution, and conduct AQP4 immunohistochemistry staining according to the routine immunohistochemistry steps.

(3) Using a microscope to scan the high-resolution image of the whole section of AQP4 immunohistochemistry.

(4) The digital process of the scanned image of AQP4 immunohistochemistry is as follows: First, calculate the ratio of the sum of AQP4 gray values of the whole section to the number of nuclei (AQP4mean). Secondly, in the immunohistochemical section, the region (ROI) with the strongest AQP4 staining intensity (that is, the region with the highest gray value of the image) is selected as the full positive expression region of AQP4. The ratio of the total gray value of AQP4 to the number of nuclei (AQP4max) in this region was calculated. Finally, the expression level of AQP4 at this biopsy point (i.e., the positive rate) was: (AQP4mean/AQP4max)*100%.

Step 9: Repeating steps 4 to 8 to obtain dynamic enhanced magnetic resonance images and stereotactic biopsy tissues of multiple glioma patients.

Step 10: Carrying out linear regression analysis on the AQP4 expression level and the average value of $k_{io}$ in all biopsy tissues to obtain the linear equation of AQP4 expression level and $k_{io}$, that is, the cell positive rate of AQP4= $(k_{io}-0.2\ s^{-1})/14.1\ s^{-1}$. The specific steps are as follows:

1. First of all, the magnetic resonance parameters (including $k_{io}$ value) of each stereotactic biopsy point in 19 patients (6 cases of WHO I-II, 13 cases of WHO of which 10 cases were recurrent gliomas) and the corresponding immunohistochemical results (i.e. AQP4 positive rate) of each stereotactic biopsy point in 45 biopsy point samples were counted one by one.

2. Secondly, the linear fitting coefficient of each magnetic resonance parameter and AQP4 expression level was evaluated by linear regression analysis. The linear equation and 95% confidence interval of the expression level of the optimal linear correlation parameters $k_{io}$ and AQP4 were obtained.

Figure 5:
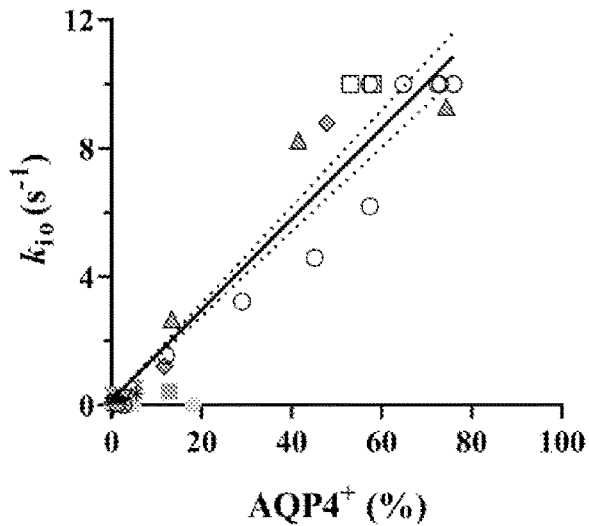
FIG. 5 shows a linear correlation is observed between $k_{io}$ and fractions of AQP4-positive cells in 45 stereotactic biopsy points from 19 glioma patients.

3. The final result is shown in FIG. 5. The linear equation of AQP4 expression level and $k_{io}$, that is, AQP4 positive rate=$(k_{io}-0.2\ s^{-1})/14.1\ s^{-1}$.

In addition, this method can also use machine learning algorithm to introduce multiple magnetic resonance parameters to establish AQP4 positive rate prediction model instead of linear regression analysis to further improve the prediction accuracy.

Step 11: According to the above linear equation, the $k_{io}$ image of each voxel in the tumor is converted into the AQP4 expression level image according to the linear formula to achieve non-invasive imaging of AQP4 expression in the tumor region.

Figure 6:
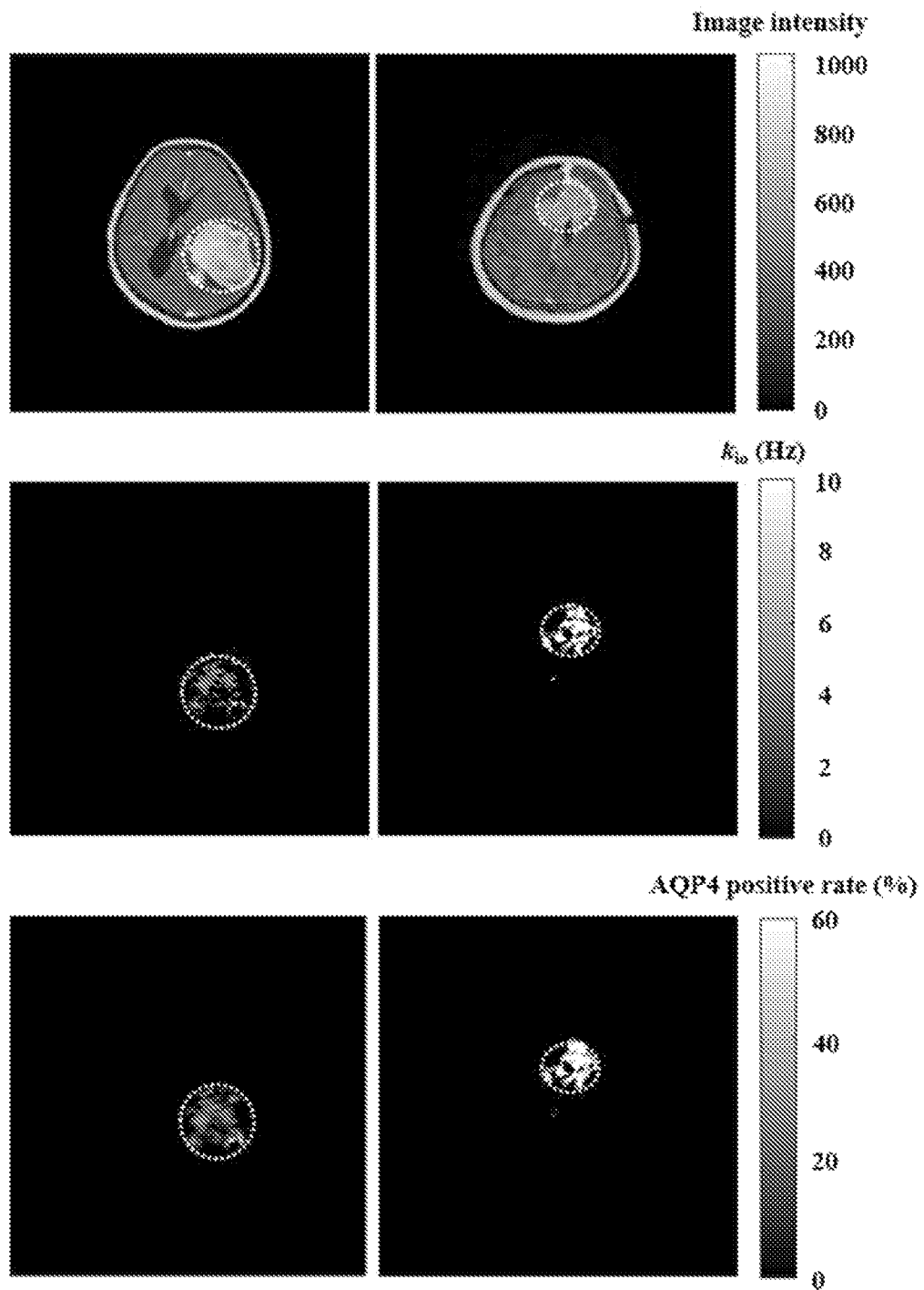
FIG. 6 shows the quantitative imaging results of AQP4 expression level in the tumor of a low-grade glioma patient (left) and a high grade glioma patient (right) generated by the embodiment.

Step 12: Repeating Step 4 to Step 6 and Step 11 for new glioma patients. Without further stereotactic biopsy, the spatial distribution of AQP4 expression in the tumor of the patient can be obtained only through magnetic resonance scanning and data analysis, as shown in FIG. 6, which is the quantitative imaging results of AQP4 expression level in a low grade glioma patient (lower left) and a high grade glioma patient (lower right), and the enhanced T1-weighted magnetic resonance images of the corresponding sections (above).

The measurement system of magnetic resonance imaging biomarker of glioma provided by the present invention includes:

Pre-processing module, performing steps 1, 2 and 3.
Image extraction module, performing steps 4 and 5.
Image processing module, performing step 6.
The post-processing module performs steps 10 and 11 in combination with steps 7, 8 and 9.
Prediction module, execute step 12.

In order to further verify the application of $k_{io}$ as a magnetic resonance imaging biomarker of gliomas in evaluating the expression level of AQP4 and in preparing products to predict the sensitivity of gliomas to radiotherapy and chemotherapy, the following experimental methods are adopted in the invention:

Cell Culture and TMZ Construction of Therapeutic Resistance Cell Model

The glioma cell lines C6 and U87MG used in the invention originate from the American Typical Cell Depository Center (ATCC, HTB14 ™). Taking C6 cell culture as an example, the method is as follows: C6 cells are cultured in Dulbecco modified Eagle medium (DMEM, Sigma-Aldrich, D6429-500 ML), which contains 10% fetal bovine serum (FBS, Biological Industries, 04-002-1A) and 1% penicillin and streptomycin double antibody (P/S, Gibco, Thermo Fisher Scientific, 10378016), that is, the complete medium. In a humidified incubator with 5% CO2+air, the temperature is 37° C. The culture medium was changed twice a week, and the cells were subcultured in the logarithmic growth phase (phase II).

C6 cells were treated with TMZ (50 μM) and treated with 50 μM TMZ dissolved in 0.1% DMSO (control group) or 0.1% DMSO in complete culture medium. The magnetic resonance parameters $k_{io}$ and physiological information (cell morphology, AQP4 expression, cell activity and cell migration distance) were obtained on the third and seventh days of TMZ (50 μM) treatment.

For primary cell cultures, glioma biopsy tissue was cut into 1 mm³ pieces and mixture with 10 ml Trypsin-EDTA (Gibco, 25200056) at 37° C. for 10-15 min until most pieces were digested into single-cell suspension. Then the cell suspensions were cultured using the same methods as the glioma cell lines.

Protocol for MRI Testing Cell Samples and Response Specific Inhibition Group

In order to obtain the cell samples for MRI, U87MG (0.5~1×10⁵) or C6 (1~2×10⁶) cell lines were first washed with DPBS, disassociated by adding 1 mL of 0.25% Trypsin-EDTA solution to 60 mm dish and incubating for 0.5 to 1.0 min, and then resuspended with 2 mL PBS (or PBS supplemented with 5 mM Gadoteridol). After centrifuging the cell sample with relative centrifugal force of 150 g at 4° C. for 5 min, the sample was resuspended in a custom MR compatible glass sample tube (diameter 5 mm×length 20 mm) with 250~300 μL PBS (or PBS+5 mM Gadoteridol). We then centrifuged the MR tubes at 300 g at 4° C. for 2 min before carrying out MRI. For AQP4 inhibition experiments, cells were pre-cultured with 6.4 μM TGN020 (Axon, CAS 51987-99-6) dissolved in PBS for 15 mins or 1 mM ouabain (Sigma, CAS 11018-89-6) for 15 mins, respectively; the PBS in the above steps was replaced with PBS+inhibitor.

In Vitro Cell Culture Desktop MRI System for Measuring Cell $k_{io}$

The 0.5 T desktop MRI measurement system for cell culture in vitro (Pure Devices GmbH, Germany) includes: the MRI system installed on the anti-vibration platform and the autonomous nuclear magnetic tube containing live cell precipitation from the incubator, 5% CO2+95% $O_2$ and PBS supernatant to ensure high survival rate, and the temperature monitoring optical fiber is installed. All MRI measurements were performed at room temperature (23.5+/−1° C.).

Before water exchange DCE-MRI, diffusion weighted imaging (DWI) was performed to localize the cell layer that showed lower apparent diffusivity using the following parameters: single-slice acquisition, slice thickness=5 mm, FOV 12.8×12.8 $mm^2$, matrix size 64×64 (zero-filled by a factor of two), 16 averages, and two b values at 10 $s/mm^2$ and 2000 $s/mm^2$. Water exchange DCE-MRI was performed with an inversion-recovery prepared turbo-spin-echo (IR-TSE) sequence and an extracellular Gd-based contrast agent, Gadoteridol (Prohance™ Bracco Diagnostics, Inc., Princeton, NJ). The following scan parameters were used in water exchange DCE-MRI: echo time (TE) 3 ms, turbo factor 16, FOV 12.8×12.8 $mm^2$, matrix size 32×32. Water exchange DCE-MRI was performed with two CA concentrations, 0 and 5 mM. At [CA]=5 mM, IR-TSE were measured with 13 IR delays (10 ms, 30 ms, 50 ms, 70 ms, 90 ms, 150 ms, 200 ms, 400 ms, 600 ms, 800 ms, 1 s, 5 s, 5 s) with repetition time TR varying together (TR=IR delay+5 s) and single repetition on each IR delay. At [CA]=0 mM, the longest IR delays were extended to 10 s with TR extended simultaneously (TR=IR delay+10 s) to guarantee full recovery of the longitudinal magnetization in each TR. The scan time for a single acquisition at [CA]=0 mM and 5 mM is 10 min and 5.5 min, respectively. Two acquisitions on [CA]=5 mM were acquired and averaged.

IR-TSE signal (M) at each IR delay was taken as the average signal of the cell pellet ROI. Then the signal was subtracted and normalized by the equilibrium magnetization ($M_0$, taken as M with the longest IR delay). We define $\overline{M}$ as the normalized signal for future SS model analysis:

$$\overline{M}=(M-M_0)/M_0 \quad (1)$$

A two-site-exchange (2SX) SS model was used here with details as described previously [6]. Briefly, the MR signal is considered as the sum of signals of two water sites—intra- and extracellular water, each site is assumed to have a similar longitude recovery rate $R_1$, with $p_i$ and $p_o$ as the mole fraction of water molecules in the intra- and extracellular space, respectively, and $p_i+p_o=1$. Then the normalized IR-TSE signal M can be described with a biexponential function, $$M=p_{sm}\exp(-tR_{1,sm})+(1-p_{sm})\exp(-tR_{1,lar}) \quad (2)$$

where $R_{1,sm}$ and $R_{1,lar}$ are the apparently smaller and larger $R_1$, respectively, and $p_{sm}$, is the apparent fraction of MR signals showing $R_{1,sm}$. The three parameters, $R_{1,sm}$, $R_{1,lar}$ and $p_{sm}$, are determined by three physical parameters including $p_i$, the intracellular water efflux rate constant ($k_{io}$), and the $R_1$ of intracellular water ($R_{1,i}$), and the CA-dependent extracellular water $R_1$ ($R_{1,o}$). For each condition (e.g., C6 at TMZ 0, 3, and 7 day), at least three samples were measured with IR-TSE at [CA]=0 mM as the baseline data. In this study, Rh were pre-determined by fitting the IR-TSE signals acquired with two different CA concentration on more than three samples in each condition.

Immunofluorescence Staining, Visualization and Quantification of AQP4 In Vitro

After the MRI tests, the cell line sample was immediately fixed by 4% paraformaldehyde (PFA) at room temperature for 20 min, then stored in 0.5% PFA (4° C.). For immunofluorescence (IF) testing, protocols following: samples were (1) blocked with 10% goat serum (Beyotime, CO265) for one hour at room temperature; (2) incubated with primary antibody overnight at 4° C. and the secondary antibody at room temperature for 1 h; (3) stained with DAPI (4',6-diamidino-2-phenylindole, Sigma-Aldrich, 1:1000) at room temperature for 5 min; and (4) washed three times with PBS. The antibody information is summarized in Supplementary Table 5. Fluorescence quantification were achieved with an Ultrafine Fluorescence Photometer (DFX, Denovix, Wilmington). Data were collected from two fluorescence channels: one in which DAPI was characterized with excitation/emission wavelengths 375 nm/435 to 485 nm and the other with either blue (excitation/emission 470 nm/514 to 567 nm) or green (excitation/emission 525 nm/565 to 650 nm) channels. Fluorescence images were taken from either a Fluorescence Inversion Microscope System (cellSensV1.13, Olympus, Japan) or a confocal laser scanning microscope (fv1200, Olympus, Japan).

Characterization of Cell Viability in TMZ Treatment

On the third and seventh days of TMZ or DMSO treatment, 1% CCK-8 (Cell Counting Kit-8, Beyotime, C0037) was added to the 96-well plate for cell viability determination. After incubation for 1 hour, the supernatant was used for the optical density test (e in FIG. 7) through a microspectrophotometer (Ultrafine Photometer, NanoDrop 2000, Thermo, Waltham).

Cell Migration Assessment

The cells were cultured into monolayer cells, and a 300-500 μm wide strip scratch was drawn from the bottom of the cell culture dish with a standard 200 ill pipette. After incubation under corresponding conditions for 24 hours, the sample was fixed in 4% PFA for 30 minutes and stained with DAPI. Only cells in the scratch area are calculated for cell migration calculation.

Labeling and Classification of Fast Circulating Cells (FCC) and Slow Circulating Cells (SCC)

The present invention uses the method of cell tracer to distinguish FCC and SCC. The OG (Oregon Green 488 Carboxylic Acid Diacetate, Succinimidyl Ester) and CTV (CellTrace™ Violet reagent, ThermoFisher scientific, Invitrogen C34557) were used to distinguish FCCs (low OG or CTV intensity) and SCCs (high OG or CTV intensity, e.g., the CTV intensity>$10^4$) in C6 cell lines and human glioma primary cell culture, respectively. Populations of FCCs and SCCs were identified and isolated in cell cultures based on their capacity to retain OG or CTV. Briefly, the cells were first suspended in PBS containing 25 μM OG and incubated in the dark at 37° C. for 10 min. After incubation, cell samples were washed in DMEM to remove residual dye and then returned to the culturing medium for three days until imaging. Before fluorescence imaging, samples were fixed in 4% PFA for 30 min and then stained with DAPI. The fraction of SCCs was defined as the fraction of OG positive cells in the DAPI positive cells. For primary human glioma primary cell cultures, the cells were stained with 5 µM CTV (the same methods as OG) for three days. Then, the cells fluorescence intensity statistics and counts were measured by a Fluorescence Activating Cell Sorter System (FACS) (LSRFortessa X-20, BD, USA).

In addition, we also used EdU (5-Ethynyl-2'-deoxyuridine), a biomarker of cells proliferation by labelling the newly synthesized DNA, to label FCCs (high EdU) and SCCs (low EdU). C6 cells were harvested and incubated with 50 µM EdU solution (Cell-Light™ EdU Apollo567, Ribobio C10338-1, including EdU solution and Apollo fluorescent solution) at 37° C. for 2 hrs, and then AQP4 was labelled following the above IF protocol. After AQP4 staining, the samples were incubated in Apollo fluorescent solution for 30 min to fluorescently label EdU and then moved for FACS test.

The cell morphology and fluorescence image of the invention are taken from the fluorescence inverted microscope system (cellSensV1.13, Olympus, Japan) or the confocal laser scanning microscope (fv1200, Olympus, Japan).
Two Rat Models of Glioma and Magnetic Resonance Measurement Methods All experimental protocols for animal studies were approved by the Animal Experimentation Committee of Zhejiang University. Adult (7~8-week-old) male Sprague Dawley (SD) rats were obtained from the Laboratory Animal Center of Zhejiang University. During glioma cell introduction, rats were anesthetized with a mixture of 2% (v/v) isoflurane in air (R500IE, RWD Life Science Co., Ltd,), and then 100 µl PBS containing $5 \times 10^6$ C6 cells and 1% antibiotics (P/S) were slowly injected under the skin at the right leg. Seven to nine days after tumour implementation, the animals were taken for 7 T MRI test and the tumour was quickly removed after and fixed for IHC after MRI.

For the orthotopic glioma model, similar protocol was followed except for that the C6 cell suspension ($0.5 \times 10^5$ cells/µl, 4~5 µl/rat, 2 µl/min) was injected into the right caudate putamen of brain using a 10 µl micro syringe at coordinates of 0.8 mm from the anterior arcuate suture, 2 mm to the right of the sagittal suture, and 4.5 mm deep. Two weeks after tumor implementation, the animals were taken for 9.4 T MRI test and were fixed with 4% PFA immediately after MRI. The maximal tumor size permitted by the institutional review board is 4000 mm³ and this limit was not exceeded in this study.
Pharmacological Specific Inhibition of AQP4 in Rat Glioma Model Here TGN020 was used to inhibit AQP4 in rat glioma model. For TGN020 group, each animal was treated with TGN020 (3 mg/kg, 4 ml/kg body weight) in the tail vein 15 minutes before water exchange DCE-MRI. In order to increase the solubility, before intravenous injection, TGN020 was repeatedly ultrasound and vortex at 37° C. to promote dissolution and dispersion in saline (0.9% NaCl). One day before TGN020 treatment, the same animal was treated with normal saline (4 ml/kg), and then water exchange DCE-MRI data collection was performed. In the control group, animals were treated with the same volume of normal saline on the first day and the second day. Here, the small volume infusion needs to be flushed after infusion to ensure the safety and treatment effect of rats.
Histology and Immunohistochemistry IHC was performed on rat glioma using paraffin embedded sections. In short, rats were euthanized with 5% isoflurane immediately after the MRI experiment, and tumor tissue was fixed with 4% PFA for 24 h. Then, after carefully matching the tumor tissue with MRI data, cut the tissue section (about 4 µM thick) along the MRI scanning section. AQP4-IHC was incubated as follows: (1) with anti-AQP4 rabbit polyclonal antibody at 4° C. overnight, and (2) with the second goat antibody HRP (horseradish peroxidase) at room temperature for 1 hour. The nucleus was stained with hematoxylin. Finally, through the microscope slide scanning system (VS120, Olympus, Japan)×Full scan tissue sections at 20 magnification.

The quantitative analysis process of immunohistochemical atlas is as follows: First, the image is stained and separated in histological imaging through ImageJ (open source Fiji v1.53c, plug-in: Color deconvolution), and further analysis is performed using MATLAB2018 (MathWorks, Natick, MA, USA) to remove the background and quantify the number of nuclei and AQP4 staining (gray intensity). Then, calculate the average AQP4 gray intensity of all cells in each slide. At the same time, several ROIs with the highest AQP4 expression were selected from all slides and manually selected by two experienced pathologists, and were considered as 100% AQP4 positive (AQP4+). Finally, the AQP4+score in each slide is further calculated as the average AQP4 gray density in this slice, and the average gray density of AQP4+% in ROI is normalized. The quantification of IHC and AQP4 follows the double-blind principle.
Region of Interest (ROI) Selection for Rat Glioma Model As most subcutaneous glioma tumours show a ring-shape of high-AQP4 expression, we used concentric donut-shape ROIs to divide both the MRI tumour regions and the corresponding histology images into six ROIs. First, we found the minimum rectangle enclosing the entire tumour and determined the rectangle centre coordinates (XR, YR), length LR, and width WR. Second, a series of concentric oval curves dividing the tumour into six ROIs were automatically drawn. The long axis (am) and short axis (bm) of concentric oval curves were calculated following, $$a_m = \begin{cases} 1/(2 \times 0.95) \times L_R & (m = 1) \\ q^{(m-1)} \times a_{m-1} & (m \geq 2) \end{cases} \quad (4)$$

$$b_m = \begin{cases} 1/(2 \times 0.95) \times W_R & (m = 1) \\ q^{(m-1)} \times b_{m-1} & (m \geq 2) \end{cases} \quad (5)$$

where m was the serial number of each curve (increasing in value from the outer (m=1)) to the inner (m=6) and q=0.75.
Water-exchange DCE-MRI and stereotactic biopsy in human glioma. (Step 7: use the biopsy planning system to obtain the best biopsy point coordinates according to the $k_{io}$ image in the tumor and combined with clinical factors).
Downstream Molecular Experiment.

Specimens obtained with the stereotactic biopsy are usually small. Nevertheless, we did some modifications in our practice for processing specimens to fit for the full spectrum of histologic, immunocytochemical, and ultrastructural studies. The 5 to 10 mm long specimens, after being removed from the biopsy needle with fine tips, were then transferred to the laboratory on a saline-soaked glass bottle to avoid drying and facilitate tissue handling. Then the biopsy specimen was divided into small samples for different purpose, for example, one may be selected for frozen storage, and the second can also be fixed in glutaraldehyde for electron microscopy. The remainder of the specimens were separately fixed and embedded and processed for routine IHC and HE stain. This method allows the performance of special staining procedures and IHC studies on comparable, consecutive specimens. Each of the serial specimens is categorized in relationship to the specific stereotactic position with the specific $k_{io}$ value. After the tissue was histologically identified with glioma by the neuropathologists, the IHC and image analysis for AQP4 and ZEB1 were performed following similar IHC protocol as rat glioma model.

As for IEM, AQP4 was detected with the immunogold-silver labelling methods as the following step: (1) fix the biopsy tissues quickly in the IEM buffer (0.2% glutaraldehyde and 2% paraformaldehyde in PBS) for 2 h at room temperature and then in PBS with 50 mM glycine for 15 min at room temperature, (2) block and permeabilize the specimens with PBS with 5% goat serum, 1% Triton, and 1% fish collagen for 40 min, (3) incubate the sample with primary antibody made in PBS with 1% fish collagen at 4° C. overnight, (4) post-embed immunogold labelling by gold-conjugated secondary antibody in the PBS containing 1% goat serum and 1% Triton at 4° C. overnight, (5) perform silver-enhancement in the dark with the HQ Silver Enhancement Assay Kit (Nanoprobes, 2012-45 ML) for visualizing AQP4 immunoreactivity, (6) rinse the sample several times with the deionized water before and after the sliver enhancement step, and (7) fix the immunolabelled specimens with 0.2% OSO4 in PBS for 2 h, stain the sample with 0.5% uranyl acetate in PBS for 1 h, dehydrate the sample in graded ethanol series, and then flat and embed the sample with Epon812 medium. Thereafter, the ultrathin sections (70 nm thickness) were observed under a Jeol-1200 electron microscope (JEOL Ltd., Tokyo, Japan).

Figure 7:
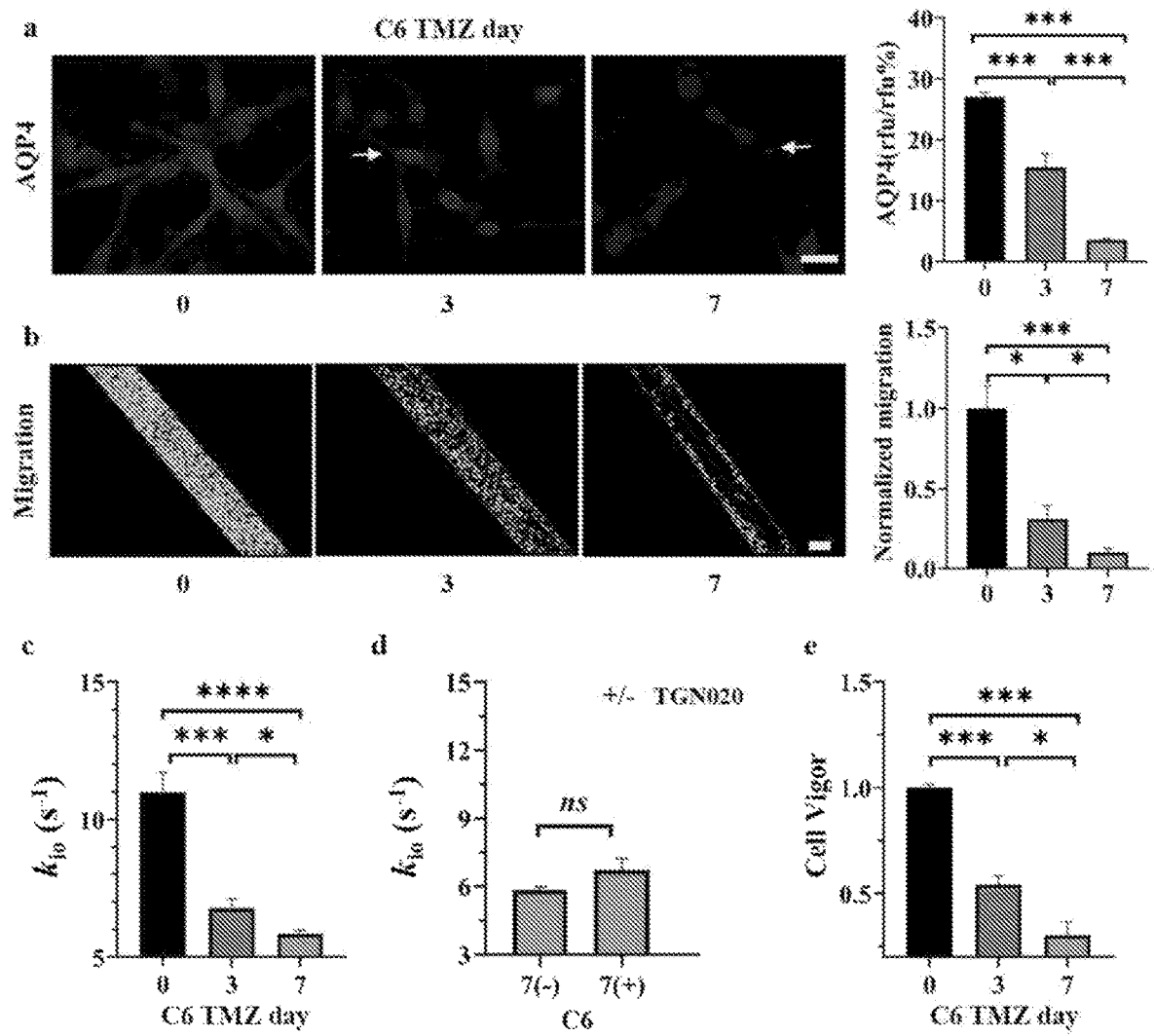
FIG. 7 shows that image biomarker $k_{io}$ can precisely detect the dynamic expression of AQP4 in C6 cell line during TMZ treatment

The Above Experiments Verify that:

$k_{io}$ can Accurately Detect the Dynamic Expression of AQP4 in C6 Cell Line During Temozolomide (TMZ) Treatment In order to evaluate the ability of water-exchange DCE-MRI to detect the dynamic change of AQP4 expression level during TMZ treatment of glioma, the invention uses the above TMZ to incubate and induce C6 cells to construct a glioma treatment model. As shown in FIG. 7a, the confocal fluorescence image shows that the expression of AQP4 continues to decrease as the time of TMZ treatment increases, and on the 7th day of TMZ treatment, the expression level of AQP4 is almost non-existent, and AQP4 is detected only in a few cell membrane cauda (a in FIG. 7. a, b, c in FIG. 8). Microfluorescence spectrophotometer (QFX, Denovix, Wilmington) was used to further quantify the expression level of AQP4, namely the fluorescence intensity (rfu), which decreased by 42.5% (p=0.0013) and 85.9% (p<0.0001) on the third and seventh days of TMZ treatment (a, right in FIG. 7), while no significant change was observed in the control group (b in FIG. 9). In addition, as expected, cell migration (scratch test, b in FIG. 7), proliferation rate (e in FIG. 9), Ki-67 expression level (d in FIG. 9), and cell viability and proliferation index (e in FIG. 7) obtained by CCK-8 (Cell Count Kit-8) gradually decreased with the increase of TMZ treatment time.

The C6 cell lines in the control group had $k_{io}$=10.9±0.7 s$^{-1}$ (n=10, c in FIG. 7) before TMZ treatment, $k_{io}$ rapidly decreased to 6.7±0.8 s$^{-1}$ (37.3%, p=0.0008, n=6) on the third day of TMZ treatment, and decreased to 5.8±0.2 s$^{-1}$ (45.5%, p<0.0001, n=7) on the seventh day of TMZ treatment (c in FIG. 7). On the 7th day of TMZ treatment, the decrease of $k_{io}$ (10.9−5.8=4.9 s$^{-1}$) was very matched with the decrease of 85% of AQP4 expression, that is, 85% of AQP4 regulated $k_{io}$=85%*5.8 s$^{-1}$=4.9 s$^{-1}$, indicating that the dynamic change of $k_{io}$ during TMZ treatment was mainly regulated by the specific regulation of AQP4 pathway. This explanation was further confirmed in the results of TGN020's specific inhibition of AQP4 in glial cells of TMZ for 7 days. The results showed that TGN020 could not further reduce $k_{io}$ because AQP4 was almost not expressed in TMZ for 7 days (d in FIG. 7).

Figure 8:
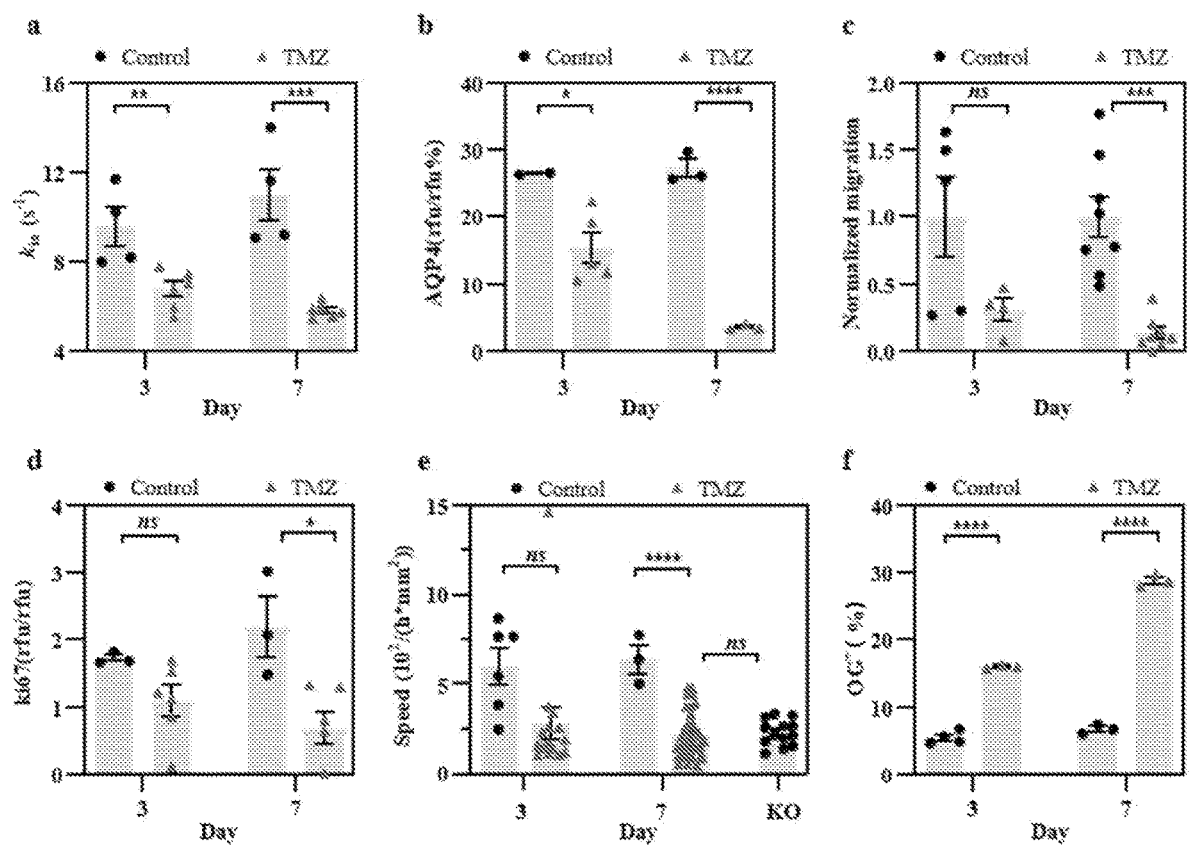
FIG. 8 shows the changes of $k_{io}$, AQP4 and other parameters of C6 cell line after TMZ treatment.
Figure 9:
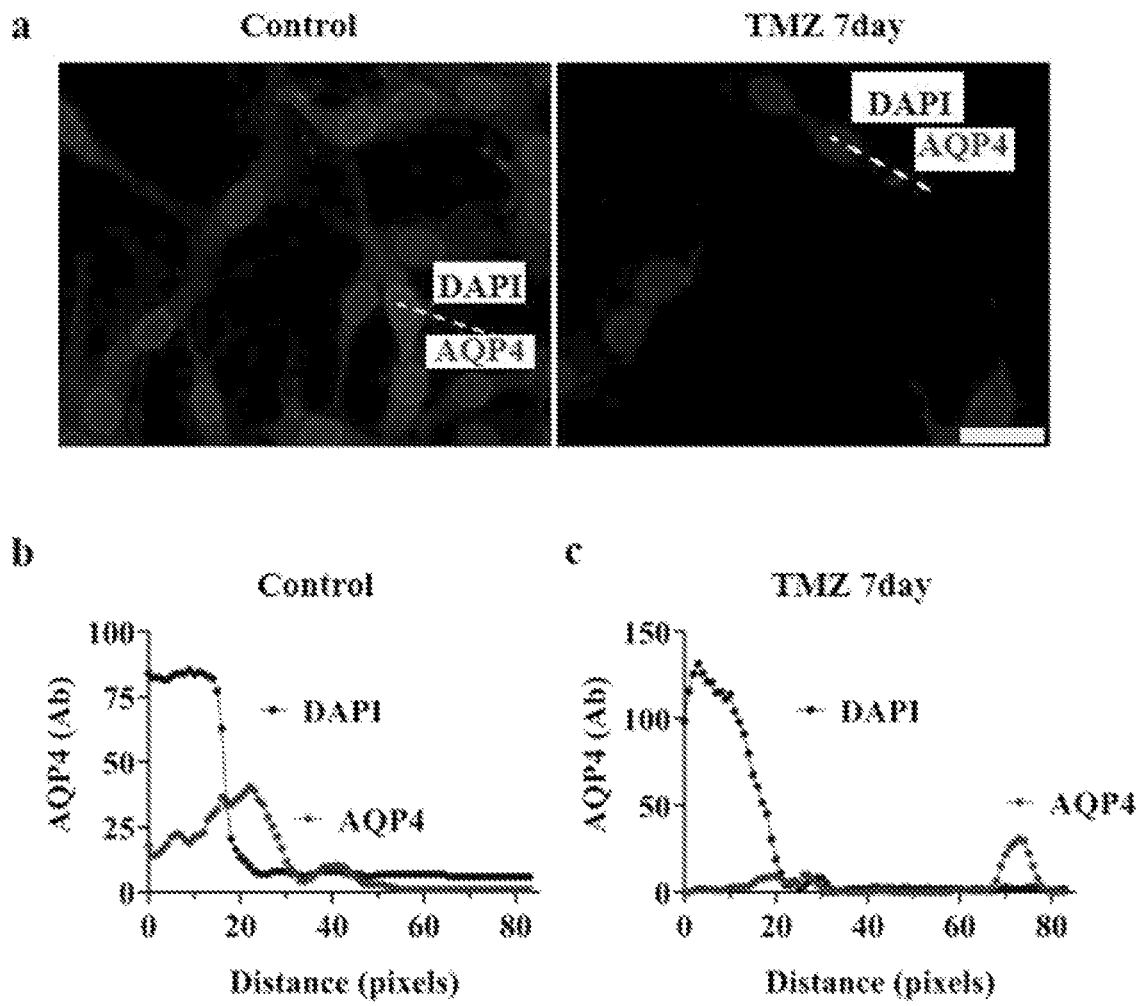
FIG. 9 shows the confocal results of AQP4 expression and distribution in C6 cell line after TMZ treatment.

Among them, the specific description of FIG. 7-9 is as follows:

FIG. 7 shows that $k_{io}$ can accurately detect the dynamic expression of AQP4 in C6 cell lines during TMZ treatment: a: After TMZ treatment of C6 cells, AQP4 (red) expression and distribution image (confocal microscope). On the right is the quantitative RFU results of AQP4 and DAPI of C6 cell line after TMZ treatment (measured by micro fluorescence spectrophotometer), n=(4, 3, 3) from left to right. Scale: 25 μM. b: The measurement results of migration ability of C6 cells at different time points after TMZ treatment showed that the nuclei labeled by DAPI (4', 6-diamido-2-phenylindole) were displayed in green in the scratch area. The bar graph on the right shows the total migration distance of all cells in the scratch area. (n=(13, 4, 7) from left to right) and standardized according to the results of the control group. Scale, 200 μm. c: In the process of TMZ chemotherapy, the dynamic change trend of $k_{io}$ in C6 cells n=(10, 6, 7), (G~I: the numbers from left to right bottom are respectively represented as the control, the third day of TMZ, the seventh day of TMZ). d: On the 7th day of TMZ treatment of C6 cells, the specific inhibition of AQP4 (marked with "+", while other cells without TGN020 were marked with "−") by TGN020 did not lead to further reduction of $k_{io}$. e: Cell viability was calculated by CCK-8 optical density (OD) (n=(4, 3, 3)). The data is displayed as mean±SEM* p<0.05, * * p<0.01, * * * p<0.001, * * * p<0.0001, ns is not significant.

FIG. 8 shows the change results of C6 cell line $k_{io}$, AQP4 and other parameters after TMZ treatment: a-f: a, $k_{io}$ change in treatment group and control group, n=(4, 6, 4, 6), p=0.0099, p=0.0006, b, AQP4 change in treatment group and control group, AQP4 (rfu)/DAPI (rfu), n=(3, 5, 3, 3), p=0.0328, p<0.0001, c, migration length of treatment group and control group (standardized by control group), n=(5, 4, 8, 8), p=0.0836, p=0.0001. d. Ki-67 (rfu)/DAPI (rfu), n=(3, 6, 3, 6), p=0.1041, p=0.0133, e, cell proliferation rate in treatment and control groups. n=(6, 15, 3, 34, 13), p=0.0505, p=0.0001. f. is the SCC score (OG+cell count/total cell count). n=(4, 3, 3, 3). Control group: C6 cell line incubated with DMSO only. In e, the results of AQP4 KO group are also shown. The data is displayed as mean±standard error* p<0.05, * * p<0.01, * * * p<0.001, * * p<0.0001, ns, not significant.

FIG. 9 shows the confocal results of AQP4 expression and distribution in C6 cell line after TMZ treatment: a, the confocal microscope image of cell morphology of AQP4 and DAPI in C6 cell line. Scale, 25 μM. b. C, the localization analysis results of AQP4 expression level on the white dotted line in a, that is, the quantitative analysis of the dynamic changes of AQP4 and nuclear fluorescence intensity at different positions far and near from the nuclear core, showed that the AQP4 expression level decreased on the 7th day of TMZ, while the highest peak of AQP4 expression was located at the position far from the nucleus, and the nuclear fluorescence showed partial highlight and irregular texture.

Figure 10:
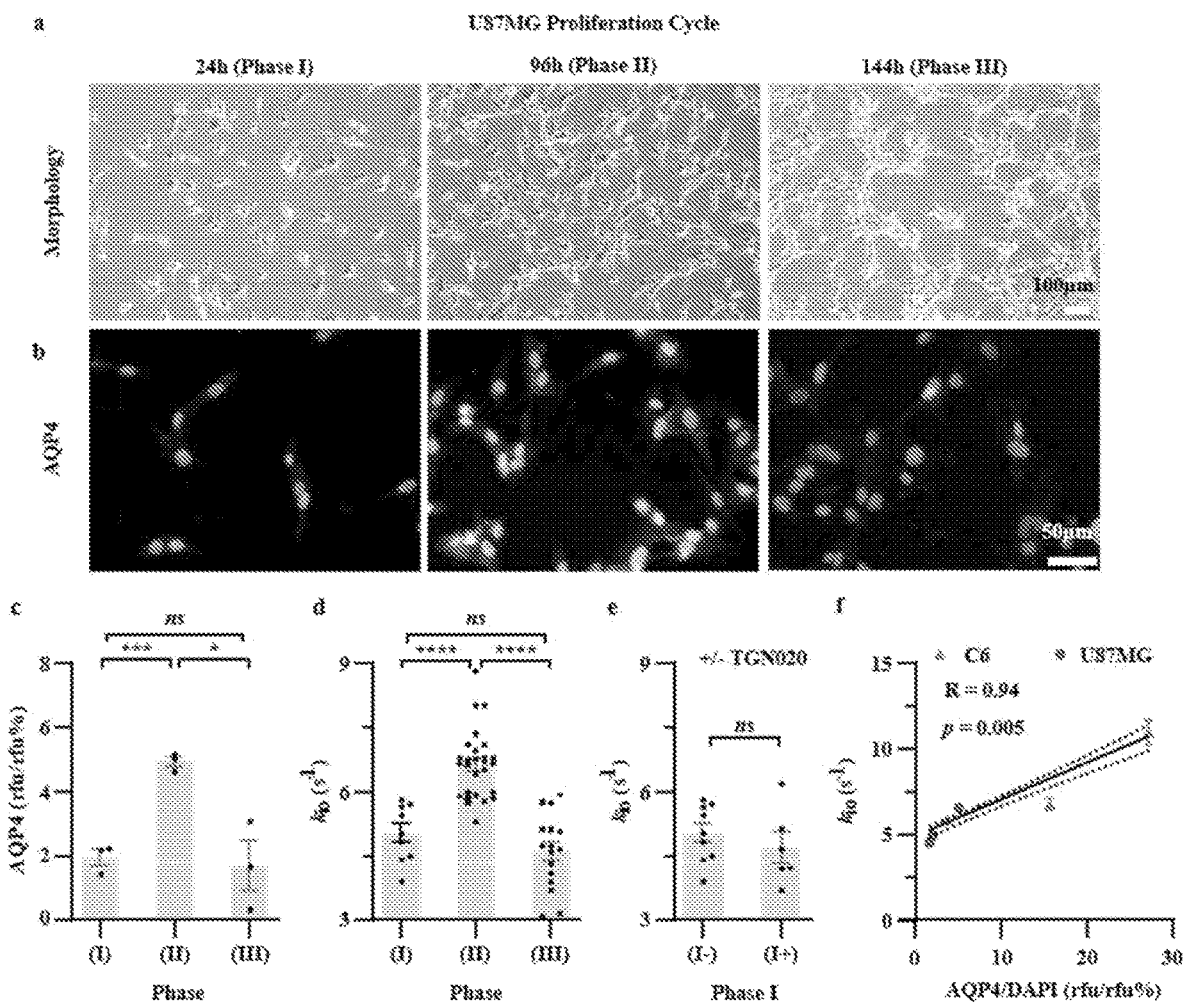
FIG. 10 shows that quantitative $k_{io}$ precisely infers the dynamic regulation of AQP4 during cell proliferation cycles.

Quantitative $k_{io}$ Accurately Infers the Dynamic Regulation of AQP4 in Cell Proliferation Cycle In order to evaluate the ability of the biomarker $k_{io}$ to detect the dynamic AQP4 regulation related to the proliferation of glioma cells, the present invention conducts SS-DCE-MRI measurement at different stages of the growth curve of U87MG, in which the cells show different proliferation states and different cell density and morphology in the cell proliferation curve (a in FIG. 10). A typical S-shaped curve of cell growth and proliferation was observed, which can be divided into (I) adaptation period (0-48 hours), in which the cells adapt to the culture conditions without division. (2) In logarithmic (log) growth period (72 hr-96 hr), the cells proliferated rapidly, resulting in a geometric exponential increase in the number of cells. (3) In the quiescent phase and the decay phase (starting from 120 hours), the overall cell proliferation slows down. The expression level of AQP4 reached its peak in Phase II, decreased by 60.4% (p<0.0001) in Phase I, and decreased by 66.0% (p<0.05) in Phase III (b, c in FIG. 10). Interestingly, but not surprisingly, $k_{io}$ showed a similar trend to the proliferation cycle: $k_{io}$ also peaked in the logarithmic phase II (6.7±0.8 s$^{-1}$, n=27, less than the previous result of using 0.1% DMSO) and decreased in the phase I (5.04±0.68 s$^{-1}$, p<0.0001) and phase III (4.6±0.9 s$^{-1}$, p<0.0001) (d in FIG. 10). In addition, in the first stage, the inhibition of TGN020 will not lead to a significant decrease in $k_{io}$ (e in FIG. 10), indicating that the disappearance of most AQP4 regulating $k_{io}$ activity in the first stage is the reason that its value is lower than that of the control group.

As shown in FIG. 10, the biomarker $k_{io}$ accurately tracks the dynamic regulation of AQP4 in the U87MG cell line in the proliferation cycle: a: The morphology of the U87MG cell line in different proliferation phases, including adaptation phase I, logarithmic phase II, static phase and recession phase III. Scale=100 μM. b: Typical microscopic results of AQP4 (red) changes in U87MG cell line. (c, d): AQP4 expression and $k_{io}$ in three cell cycle stages. e: Inhibition of AQP4 with TGN020 (n=6) will not lead to further reduction of $k_{io}$ in Phase I. In c-e, the bar height and error bar width represent the average value and standard error, respectively, * p<0.05, * * * p<0.001, ns is not significant, p=0.7767 in c, p=0.2207 in d, p=0.4031 in e. In c-e, the data points (such as the point map) cover the corresponding boxes, and the bilateral unpaired t test f: use the data from U87MG and C6 cell lines to analyze the correlation between the expression of $k_{io}$ and AQP4. Each cell line uses the same symbol (C6 is triangle, U87MG is point), the solid line reflects linear regression, and the area between the two dotted lines reflects 95% confidence interval.

Biomarker $k_{io}$ is Linearly Correlated with AQP4 Expression in C6 and U87M Cell Lines In order to further evaluate $k_{io}$'s ability to quantify AQP4 expression, a direct correlation analysis was performed between $k_{io}$ and AQP4 expression (rfu value, see AQP4 fluorescence spectrophotometer for detection method). In FIG. 10, f, $k_{io}$ and AQP4 show a significant positive correlation (correlation coefficient R=0.92, p=0.01), which indicates that $k_{io}$ can accurately represent the dynamic expression of AQP4 even in glioma cell types.

In vivo $k_{io}$ map obtained from water exchange DCE-MRI can accurately reveal the heterogeneity of AQP4 within and between tumors in rat glioma model In order to further prove the accuracy of water exchange DCE-MRI in detecting AQP4 in vivo, C6 cell line was subcutaneously implanted into the right leg of Sprague Dawley (SD) rats to establish a glioma animal model. In vivo water exchange DCE-MRI is achieved through clinical use of Gd-based CA (dimethylamine gadolinate, Guangzhou, China). In order to better estimate $k_{io}$, the invention uses the method of two injections of CA, which improves the accuracy of $k_{io}$ estimation by 10 times compared with the traditional method of single injection of contrast agent. In addition, the steady-state multi-gradient echo (MGE) sequence is used to overcome the potential T2* artifacts caused by contrast agents. Combined with numerical simulation, the MGE sequence parameters are optimized (for example, the optimal parameters: repetition time (TR) =100 ms and turning angle)(FA)=20°. Finally, the fitting error of SS model is carefully analyzed to remove $k_{io}$ with large fitting error. In conclusion, these steps ensure the accuracy of water exchange DCE-MRI in estimating $k_{io}$ in the physiological range ([0 s$^{-1}$, 10 s$^{-1}$]) (c in FIG. 11).

As expected, for most tumor voxels, the in vivo SS model fits well. The $k_{io}$ diagram (d in FIG. 11) and the AQP4 immunohistochemical (IHC) staining diagram (e, fin FIG. 11) of the corresponding sections show similar spatial distribution. In addition, strong intratumoral heterogeneity of AQP4 expression was observed in most animals, which showed high expression at the tumor edge (invasion area) and low expression in the tumor core (e, fin FIG. 11). The $k_{io}$ map shows the same expression pattern as AQP4, for example, the high $k_{io}$ at the edge of the tumor and the low $k_{io}$ in the core of the tumor in the schematic diagram. In order to verify the accuracy of quantitative evaluation of AQP4 expression measurement by water exchange DCE-MRI in vivo, combined with the circular distribution of AQP4 in most glioma subcutaneous model animals, a series of concentric ring-shaped ROI was used to divide the tumor section into six regions (method, d, e in FIG. 11). Then calculate the average $k_{io}$ value and AQP4 positive (AQP4±) score of each ROI. The results showed that the $k_{io}$ map obtained from water exchange DCE-MRI had a strong linear correlation with the AQP4+score of each animal (i in FIG. 11, correlation coefficient of each animal R>0.80, FIG. 12) and the average R=0.82 (p<0.0001, g in FIG. 11, n=10). These results show that $k_{io}$ can accurately detect the heterogeneity of AQP4 expression in glioma in vivo. Linear regression analysis (g in FIG. 11) further shows that the $k_{io}$ associated with AQP4 is as high as 10.5 s$^{-1}$, while the $k_{io}$ through non-AQP4 pathway is only 0.4 s$^{-1}$. The fraction of AQP4±cells (AQP4±%) in each ROI (a total of 60 ROIs) is linear:

$$k_{io}=10.5s^{-1}*AQP4^{+}\%+0.4s^{-1}$$

Figure 11:
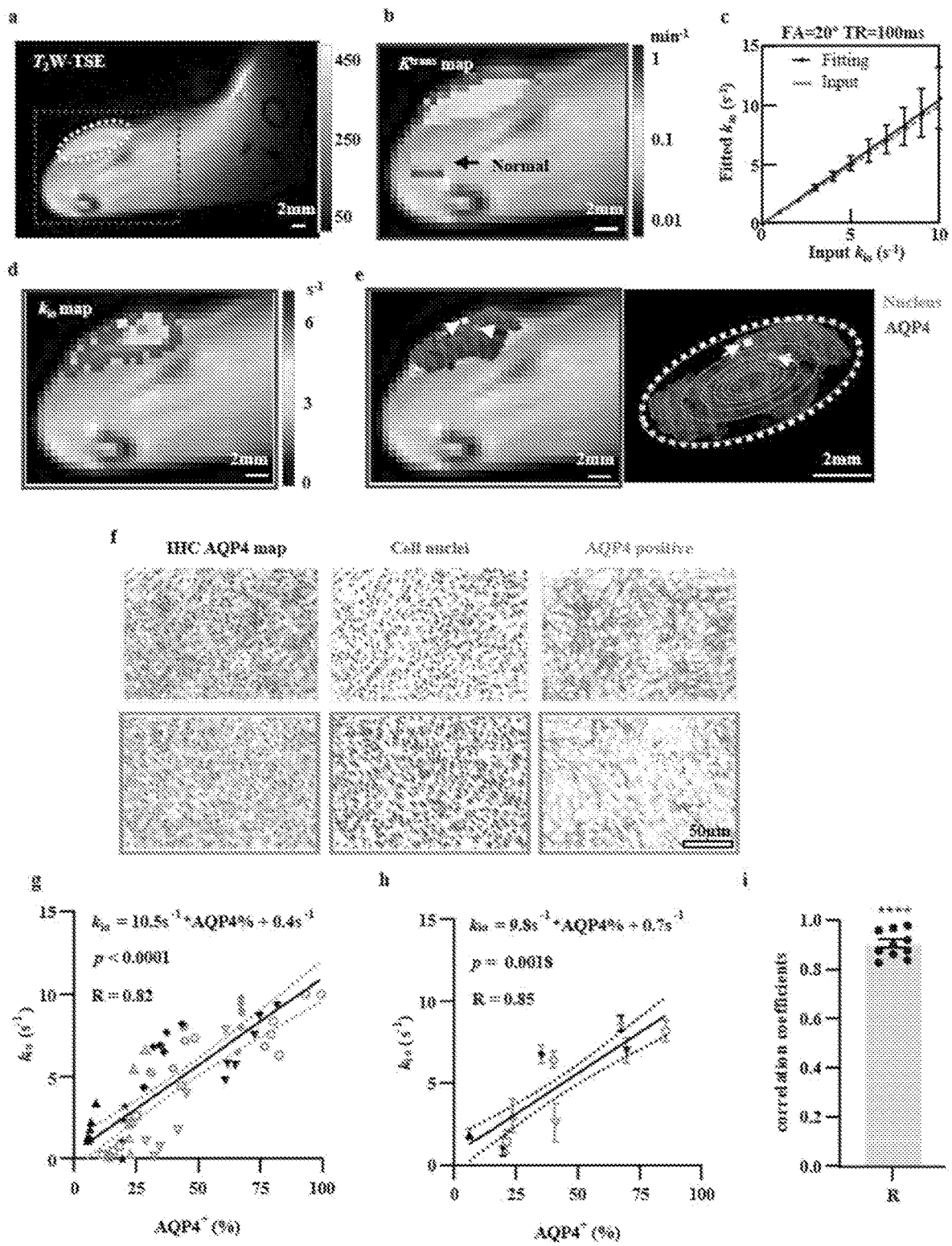
FIG. 11 shows the $k_{io}$ diagram obtained by water exchange DCE-MRI, which can accurately reveal the heterogeneity of AQP4 in vivo.

As shown in FIG. 11, the $k_{io}$ image obtained by water exchange DCE-MRI can accurately and accurately reveal the heterogeneity of AQP4 in vivo: a: T2-weighted TSE image of glioma xenograft, red and blue rectangles represent FOV in b and d respectively. b: $K^{trans}$ image superimposed on T2 weighted TSE image. c: Monte Carlo simulation shows that the optimization of MRI parameters (FA=20° and TR=100 ms) ensures that the water exchange DCE-MRI is within the physiological range ([0 s$^{-1}$, 10 s$^{-1}$]). The dotted line indicates the input $k_{io}$ (ground reality). The point and error line represent the average and standard deviation of the estimated $k_{io}$, n=(100, 100). d: $k_{io}$ map superimposed on T2 weighted TSE image. e: The IHC results of all slices d are superimposed on the T2-weighted image (left) and not superimposed (right). Here, AQP4 and nucleus are marked with different colors. In each animal, six contour lines were used to divide the tumor section into six concentric ring-shaped ROI. f: The enlarged IHC comes from a tumor ring pixel (upper part of f) and a tumor core pixel (lower part of f). Its position is described in (d, e). From left to right, they are the merged image, nucleus and AQP4. g: A linear correlation was observed between the ROI average $k_{io}$ and AQP4 positive scores of 60 ROIs (6 ROIs per animal, n=10, data from the same animal displayed with the same symbol). h: This linear correlation still exists between the average $k_{io}$ of the whole tumor and the AQP4 positive score (n=10, each animal uses the same symbol as g). In g and h, the solid line reflects the linear regression, and the area between the two dotted lines reflects the 95% confidence interval. i: Statistical data of correlation coefficient in intratumor correlation analysis between $k_{io}$ and AQP4+score of each animal (n=10, black spot). The bar height and error bar width represent the average value and standard error respectively**** p<0.0001, two-sided t test of Z-transform correlation coefficient.

When the average expression of $k_{io}$ and AQP4 in the whole tumor of each animal is used for analysis at the level of tumor, the linear relationship between $k_{io}$ and AQP4 expression still exists (h in FIG. 11). In combination with $k_{io}$ in FIG. 12, the expression level of AQP4 in each rat glioma model can be accurately displayed (good correlation), indicating that $k_{io}$ can accurately measure the intra-tumor and inter-tumor AQP4 heterogeneity.

Figure 12:
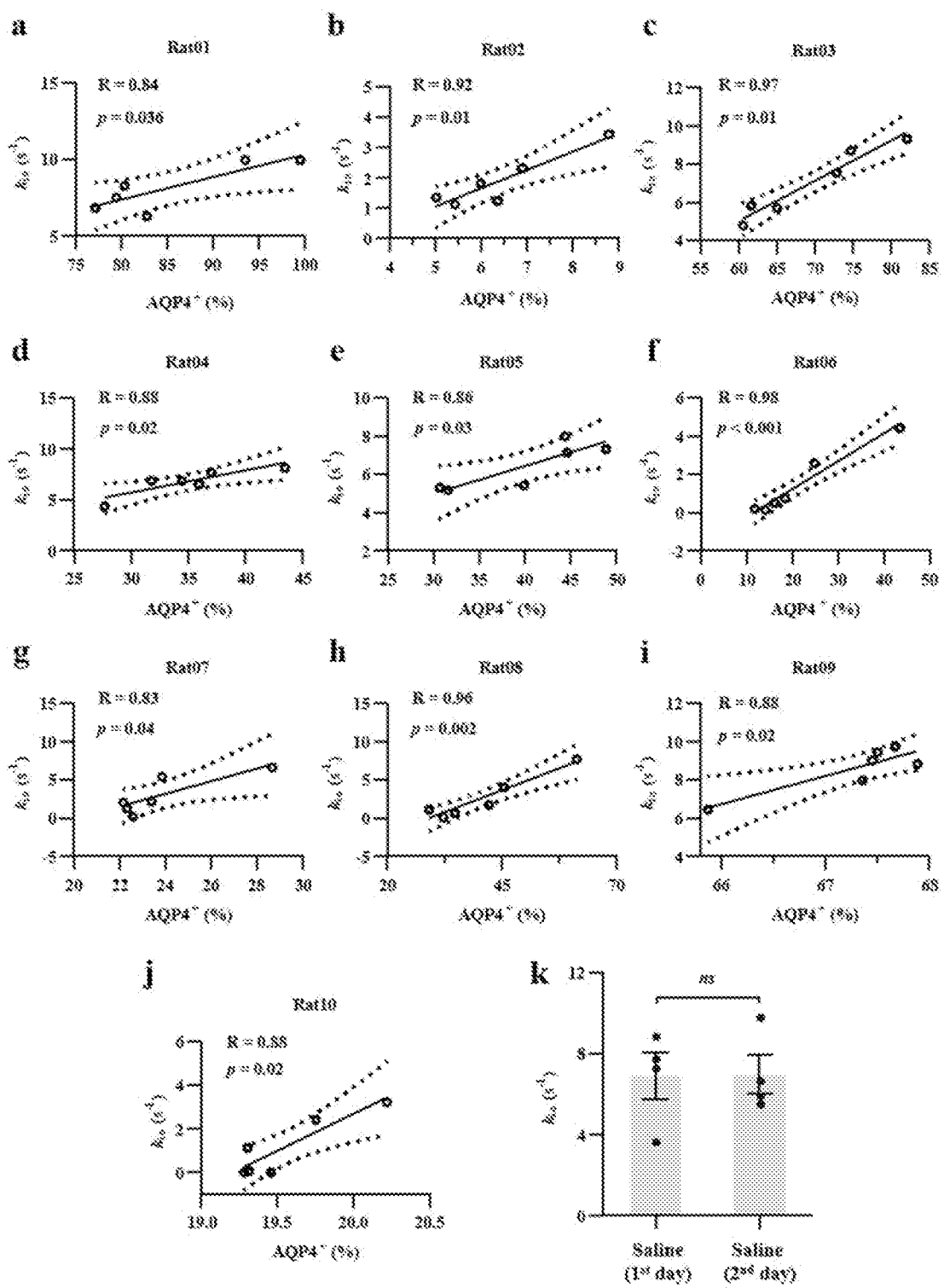
FIG. 12 shows that $k_{io}$ can accurately display the expression level of AQP4 in each rat glioma model.

As shown in FIG. 12, $k_{io}$ can accurately display the expression level of AQP4 in each rat glioma model: a-j: the significant linear correlation between $k_{io}$ value and AQP4+ percentage in each experimental animal. Here, considering the circular distribution of AQP4, each tumor section (including tissue section and MRI scan section) is divided into six concentric circular regions using a series of concentric elliptical ROI. Correlation analysis was performed by using the mean value of $k_{io}$ in 6 regions of each rat and its corresponding 6 AQP4+ percentages. k. In the control group with TGN020 specific interference (FIG. 12), the average $k_{io}$ of the whole tumor showed no significant change between two days after the injection of normal saline. paired t test, ns was not significant, p=0.9588. The bar height and error bar width represent the average value and standard error of the average value respectively. n=4.

The invention also constructs a glioma model in situ by implanting C6 cell line into the right caudate putamen of SD rats, and obtains water exchange DCE-MRI data. Because the tumor size in the glioma in situ model (a, b in FIG. 13) is much smaller than that in the subcutaneous glioma model, and the spatial resolution of MRI is limited, only the correlation analysis between the expression of $k_{io}$ and AQP4 in rats with glioma in situ is performed. As expected, a linear correlation was observed between the average expression level of $k_{io}$ and AQP4 in the whole tumor (R=0.92, p<0.01, n=7, c in FIG. 13). In addition, the $k_{io}$ of AQP4 regulation and non-AQP4 regulation determined by linear regression were 13.0 s$^{-1}$ and 1.3 s$^{-1}$, respectively, which were very close to the corresponding values in the subcutaneous glioma model. These results further proved the robustness of $k_{io}$ as an imaging biomarker of AQP4 expression in glioma.

Figure 13:
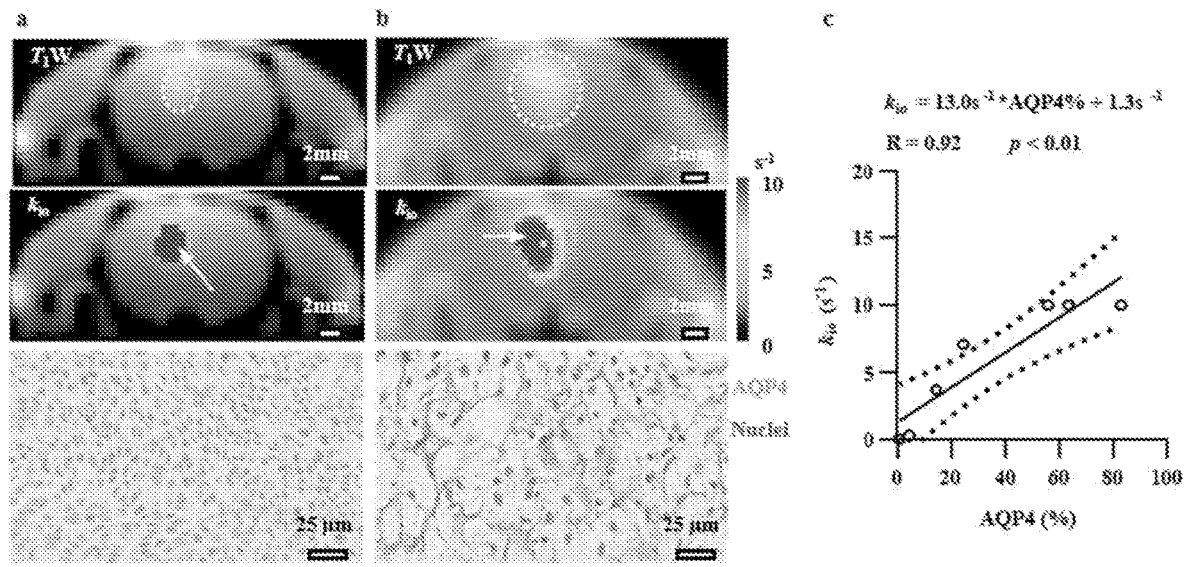
FIG. 13 shows that a linear correlation between the expression of AQP4 and $k_{io}$ in the rat model of C6 glioma in situ.

As shown in FIG. 13, a linear correlation between the expression of $k_{io}$ and AQP4 was observed in the rat model of C6 glioma in situ: a, b: $k_{io}$ map from two animals with low $k_{io}$ (a) and high $k_{io}$ (b) and typical IHC results of AQP4. From top to bottom are the typical IHC results of contrast-enhanced T1-weighted image (the tumor position is represented by a white dotted circle), $k_{io}$ image superimposed on the T1-weighted image and AQP4 with white arrow pointing to the position. MRI scale: 2 mm. IHC scale: 25 μM c: Linear correlation was observed between the total tumor mean $k_{io}$ and AQP4+ score in 7 rats with glioma in situ. The solid line reflects the linear regression analysis, and the two dotted lines represent the 95% confidence interval. n=7.

Figure 14:
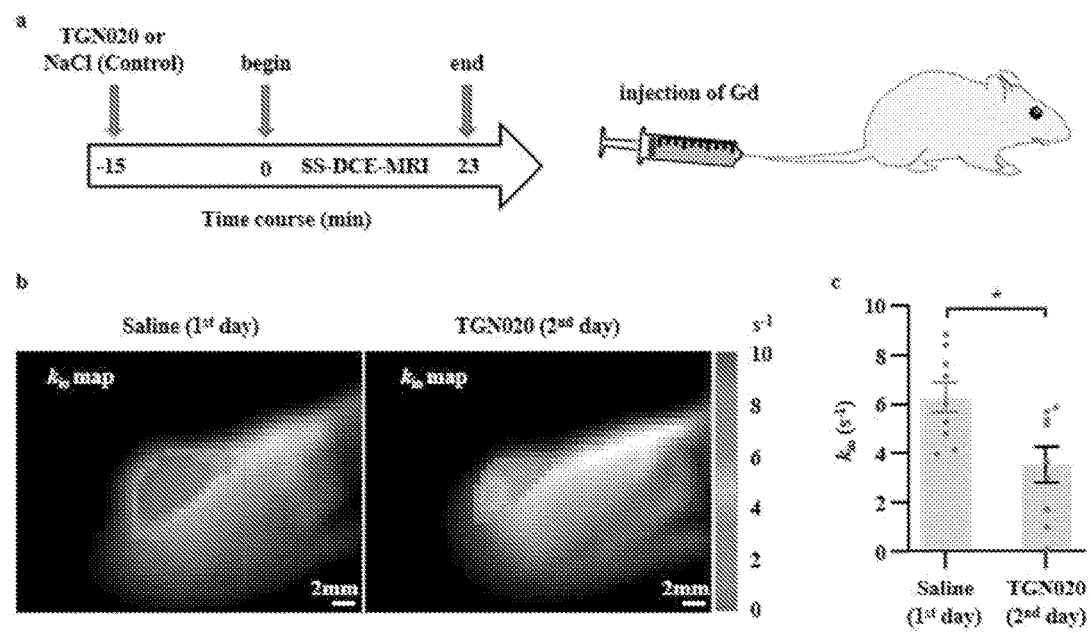
FIG. 14 shows effect of pharmacological inhibition of AQP4 on $k_{io}$ in the subcutaneous rat glioma model.

Pharmacologically Specific Inhibition of AQP4 can Reduce $k_{io}$ in Rat Glioma Model In order to further verify that water exchange DCE-MRI is a sensitive imaging method related to AQP4 expression in vivo, TGN020 was further used to specifically inhibit AQP4 function in rat subcutaneous glioma model. As shown in FIG. 14, TGN020 (3 mg/kg, dissolved in saline) was injected through the tail vein 15 minutes before each animal (n=9) was scanned for water exchange DCE-MRI. Selecting the injection time of TGN020 can ensure that TGN020 reaches and maintains a stable uptake level during the water-exchange DCE-MRI acquisition process. As the control group, compared with the day before the treatment of TGN020, the same animal was used with the same volume of normal saline instead of TGN020 for water exchange DCE-MRI measurement. The results showed that the glioma treated with TGN020 showed a significant decrease in the $k_{io}$ value, as shown in the $k_{io}$ diagram (b in FIG. 14), the average $k_{io}$ of the whole tumor showed a significant decrease from 6.3±0.6 s$^{-1}$ (injection of normal saline group) to 5±0.7 s$^{-1}$ (injection of TGN020 group) (43%, n=9, p=0.0246, c in FIG. 14). In addition, TGN020 also slightly reduced the average $K^{trans}$ of the whole tumor from 0.060±0.015 min$^{-1}$ (normal saline) to 0.045±0.024 min$^{-1}$ (TGN020), which has no significant impact on $k_{io}$ estimation, because most tumor voxels can still pass error analysis and produce reliable $k_{io}$ measurements (see the example of b in FIG. 14). In the control group, each animal (n=4) was treated with saline on the first day and the second day, and there was no significant change in $k_{io}$ in these two days (k in FIG. 12). Although for safety reasons, the dose of TGN020 used here is relatively small, and because TGN020 can only partially inhibit AQP4, $k_{io}$ is not completely inhibited by TGN020. However, the current qualitative results can well prove the sensitivity and specificity of $k_{io}$ as a biomarker of AQP4 expression level in glioma.

As shown in FIG. 14, the effect of specific drug intervention inhibition of AQP4 on $k_{io}$ in subcutaneous rat glioma model: a: animal experimental timeline and schematic diagram, showing the experimental course of the effect of AQP4 specific inhibitor (TGN020) on $k_{io}$ in vivo. For TGN020 group, the same animal was injected with normal saline on the first day and TGN020 on the second day. For the control group, animals were injected with normal saline on both days. b: The effect of AQP4 inhibition on glioma (C6) in TGN020 group was demonstrated by using the $k_{io}$ map registered on the T2-weighted TSE image. Ruler: 2 mm. c: After inhibiting AQP4 with TGN020, the average $k_{io}$ of the whole tumor decreased by 43% (from 6.3±0.6 s$^{-1}$ to 3.5±0.7 s$^{-1}$). Bilateral paired t-test, * p<0.05, where p=0.0246. The data points cover the corresponding boxes, and the bar height and error bar width represent the average value and standard error respectively, n=9.

$k_{io}$-Guided Stereotactic Biopsy of Human Glioma Further Verified the Linear Correlation Between $k_{io}$ and AQP4 Expression Water exchange DCE-MRI revealed the intratumoral heterogeneity of $k_{io}$ in human gliomas by injecting clinically approved contrast agent (Gd-DTPA, 0.1 mmol/kg body weight). The invention aims to use $k_{io}$ instead of AQP4 spatial distribution to guide stereotactic biopsy. It is well known that brain transfer during surgery may affect the sampling accuracy of frameless neural navigation technology. This is unlikely to affect the spatial accuracy of radiopathology correlation. The invention avoids the influence of brain metastasis from preoperative MRI to tumor sampling time through frame stereotactic biopsy technology. Therefore, it is expected that the quantitative analysis of $k_{io}$ images and biopsy samples will produce highly reliable evaluation, which will allow accurate interpretation of radio-histopathology related results at the voxel level.

The present invention belongs to observational research, and has been approved by the Institutional Review Committee (IRB) of Shandong Provincial Hospital Affiliated to Shandong First Medical University, with the written informed consent of each subject. From May 2019 to August 2021, 21 suspected glioma patients were recruited according to the IRB inclusion criteria (histology and molecular diagnosis were confirmed by biopsy), and Leksell was used ® Model G Stereotactic Frame System (Elekta AB, Stockholm, Sweden). Before biopsy, water exchange DCE-MRI was performed to obtain $k_{io}$ map (c in FIG. 15). Then, the $k_{io}$ value is combined into the structural image used to guide the stereotactic biopsy, and multiple ROIs with different $k_{io}$ values are collected in each patient (a in FIG. 15). After filtering out 2 patients with poor image registration, the final analysis used 45 biopsies from 19 patients (6 WHO I-II, 13 WHO 10 of which were recurrent gliomas).

Figure 15:
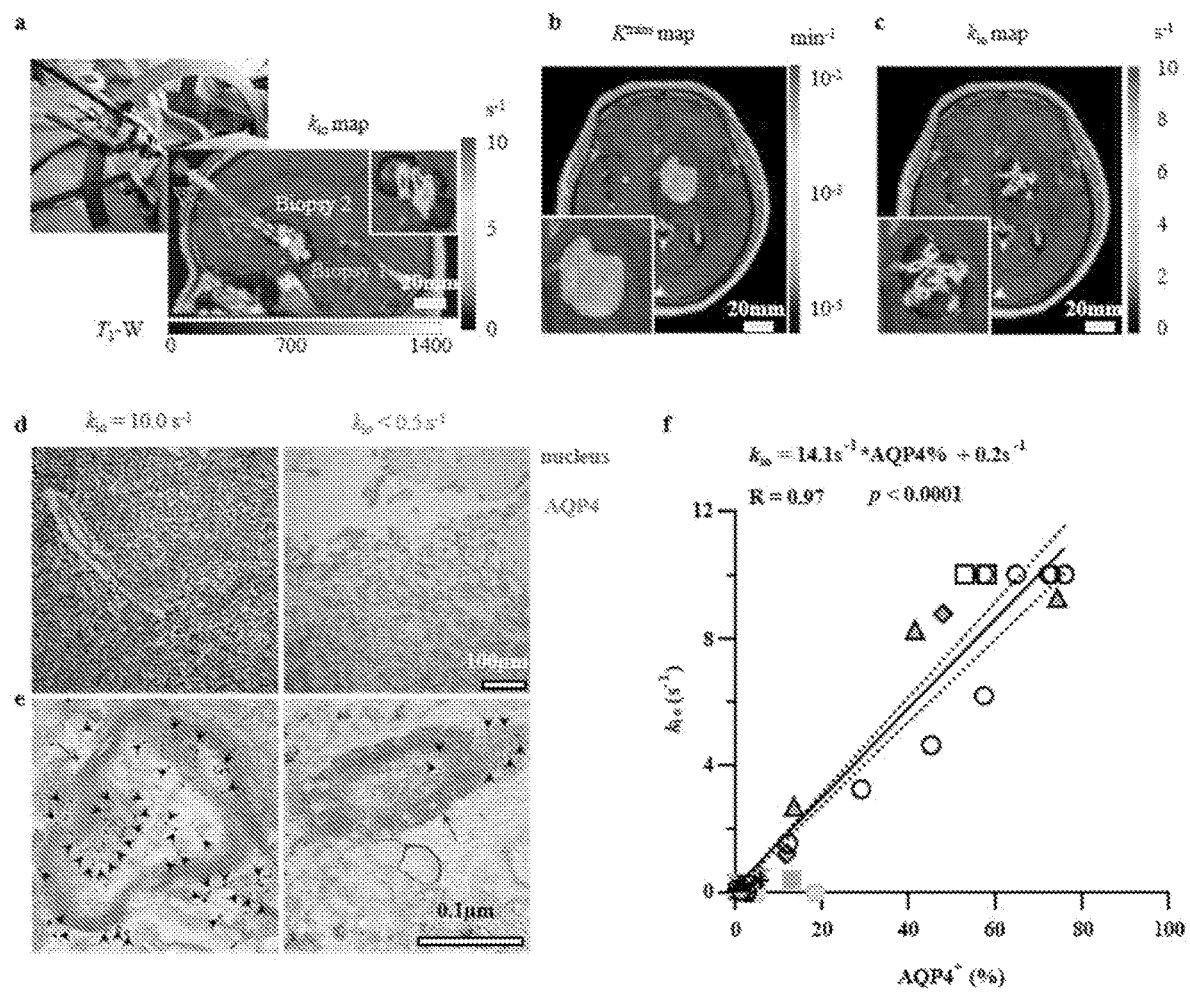
FIG. 15 $k_{io}$ map obtained from water-exchange DCE-MRI reveals intratumoural AQP4 distribution in human glioma.

The typical $K^{trans}$ and $k_{io}$ parameters of the same section of a patient are shown in b and c in FIG. 15, where $K^{trans}$ and $k_{io}$ show different spatial distribution, indicating different pathophysiological conditions. As shown in d in FIG. 15, the AQP4-IHC results of typical biopsy samples, where the samples with $k_{io}$=10.0 s$^{-1}$ show higher AQP4 expression than the samples with $k_{io}$<0.5 s$^{-1}$. The in situ ultrastructural detection results of the combination of IHC and AQP4 antibody immunoelectron microscopy (IEM) based on transmission electron microscopy (TEM) also showed that the density of AQP4 positive gold nanoparticles in the biopsy samples with high $k_{io}$ was high, which supported the conclusion of this paper at the subcellular level (e in FIG. 15). The AQP4+score in each biopsy was further quantified, and all 45 biopsy samples were summarized. It was found that there was a significant linear correlation between $k_{io}$ and AQP4+cell score (R=0.97, p<0.0001) (f in FIG. 15). The linear regression equation is as follows $$k_{io}=14.1s^{-1}\times AQP4^{+}\%+0.2s^{-1}$$

This shows that the $k_{io}$ associated with AQP4 (14.9 s$^{-1}$) is much larger than that associated with non-AQP4 (that is, $k_{io}$ baseline, 0.2 s$^{-1}$), and in human gliomas, $k_{io}$ is mainly controlled by the pathway regulated by AQP4. This linear relationship between the expression of $k_{io}$ and AQP4 still exists in multiple biopsy samples collected for the same patient, as shown in f in FIG. 15, where the data from each patient is marked with different symbols.

As shown in FIG. 15, the $k_{io}$ map obtained from water exchange DCE-MRI revealed the distribution of intratumoral AQP4 in human glioma: a: The $k_{io}$ guided stereotactic biopsy was used to verify the $k_{io}$-AQP4 relationship in human glioma. Multiple biopsies with different (high or low) $k_{io}$ signal intensities were obtained from 19 patients with glioma. A schematic map is shown here ($k_{io}$ map is covered on the 70th frame of water exchange DCE-MRI), in which two points are collected with the same needle and the image of the stereotactic biopsy system. (b, c): The $K^{trans}$ diagram b and $k_{io}$ diagram c of the same patient shown in Figure a are registered on the water-exchange DCE-MRI image (frame 70), (a, b, c, scale: 20 mm). (d, e): typical examples of AQP4 IHC (d, scale 100 µM) and IEM (e, scale 0.1 µM) with high (left) and low (right) $k_{io}$ stereotactic biopsy respectively. In IHC, AQP4 is labeled brown and the nucleus is labeled blue. In IEM, AQP4 is marked with gold particles (black arrow). The red arrow represents glial microfilament. In these two results, higher AQP4 expression was observed in the tissues with larger $k_{io}$, and vice versa. f: A linear correlation between $k_{io}$ and AQP4+cell fraction was observed in 45 stereotactic biopsy sites from 19 patients with glioma. Each patient's data is marked with different symbols. The solid line reflects the linear regression analysis, and the two dotted lines represent the 95% confidence interval.

Figure 16:
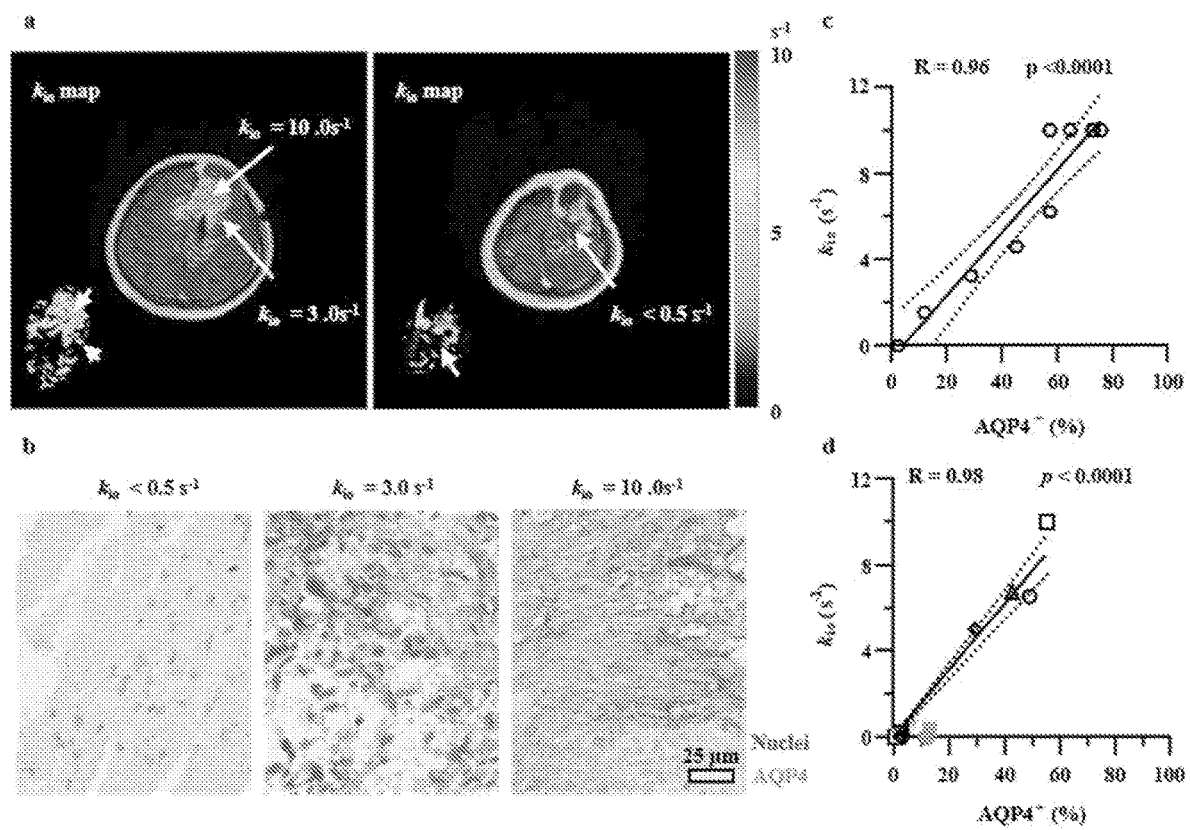
FIG. 16 shows the special cases and sample average statistics of patients with glioma.

FIG. 16 also shows a special case of recurrent glioblastoma, which was treated by radiofrequency ablation with multiple needles due to the large tumor area. In this special case, the doctor collected 10 biopsy samples safely along the planned track. The invention also observed a good linear correlation between $k_{io}$ and AQP4 in 10 biopsy samples (R=0.96), which further proved the accuracy of $k_{io}$ in measuring AQP4 in single application. In addition, if all the biopsy data of each patient are averaged, it is found that there is a good correlation between the average $k_{io}$ and the average AQP4 of the biopsy samples (R=0.98, d in FIG. 16).

As shown in FIG. 16, the statistical data of the special cases and samples of patients with glioma: this is a patient with recurrent glioblastoma. Because of the large tumor area, he has received multi-point biopsy surgery. In this special case. Ten biopsy samples were collected safely along the planned trajectory of the needle. a: Examples of $k_{io}$ atlas and the location to obtain biopsy samples (white arrow). b: An example of AQP4 IHC results at three biopsy sites is shown in a. Scale: 25 µM c: A linear correlation between $k_{io}$ and AQP4+cell fraction was observed in 10 stereotactic biopsy sites of the patient. d: The linear correlation between the average $k_{io}$ and AQP4+cell score of 19 data points from 19 patients remained unchanged. Here, for a patient who has obtained multiple biopsies, the average result of all biopsies of the patient is used as the final representative biopsy result of the patient. The solid line reflects the linear regression analysis, and the two dotted lines represent the 95% confidence interval.

In summary, the above experiments from the level of cultured cells in vitro, the animal level of two rat models of glioma in vivo and the clinical cases of human glioma cases show that $k_{io}$ is a powerful and sensitive imaging biomarker of AQP4 in human glioma.

Low $k_{io}$ Reflects the Treatment Resistance of Glioma

The recurrence of glioma is common after radiotherapy. We found that the cells with low $k_{io}$ (i.e. low AQP4) may represent the cell subtype of treatment resistance in glioma. Careful observation of C6 nuclear image texture after TMZ treatment showed that some cells showed nuclear damage after TMZ treatment, while others showed basically complete and uniform nuclear structure, indicating that these cell subtypes have resistance to nuclear damage type anticancer drug TMZ (a in FIG. 17). The expression of AQP4 in these anti-TMZ chemotherapy cells was significantly lower than that in cells sensitive to TMZ treatment (c in FIG. 17). On the other hand, during TMZ treatment, it was also observed that the number of static and slow proliferating cells (SCC) increased at the same time, indicating that these cells were more resistant to TMZ than fast proliferating cells (FCC) (b in FIG. 17). Here, SCC is labeled by the above cell fluorescence tracing method (see method), in which SCC uses CellTrace reagent (Oregon Green (OG) for C6 cell line and CellTrace Violet (CTV) for human glioma primary cells) to label the positive cells (OG+ and CTV+). Because SCC does not undergo division and proliferation, it retains more OG and CTV fluorescent dyes, which presents a bright image under the microscope. On the third and seventh days of TMZ treatment, the proportion of SCC increased from 6.0 (±0.4)% before TMZ treatment to 16.0 (±0.1)% (p<0.0001) and 28.9 (±0.3)% (d in FIG. 17 and f in FIG. 9), respectively. In order to further prove the close coupling between AQP4 expression and cell cycle, on the 7th day of TMZ chemotherapy, EdU (5-Ethynyl-2 deoxyridine) was used to rapidly label the newly synthesized DNA to mark the proliferating C6 cells while double-staining AQP4. The corresponding flow cytometry results showed that the expression of AQP4 in SCC (low EdU) cells was lower than that in FCC (e in FIG. 17), and vice versa. Some new long-tailed structures or 'pseudopods' (red arrows) were found in the morphological images of C6 cells on the seventh day of TMZ treatment (b in FIG. 17). These features are also often considered as a kind of stem cell-like characteristics of treatment resistance. Therefore, lower $k_{io}$ (i.e. AQP4) is often associated with more SCC subtypes, lower proliferation rate and treatment resistance phenotype (e, f in FIG. 17).

More importantly, the use of the biomarker ZEB1 (zinc finger enhancer binding protein 1, a transcription factor that regulates DNA damage) further characterizes the anti-treatment status of clinical glioma biopsy samples (the immunohistochemical method and quantitative method are the same as AQP4). ZEB1 has been used as a biomarker of glioma treatment-resistance. We found that the lower $k_{io}$ biopsy samples of recurrent gliomas had higher ZEB1 expression than the biopsy samples of higher $k_{io}$ from the same subject (f in FIG. 17), further indicating that the lower $k_{io}$ might represent the subtype of treatment-resistant gliomas. The flow cytometry results of primary cell cultures from biopsy samples (see method) (g in FIG. 17) further support this conclusion, in which cells from low $k_{io}$ samples show a higher proportion of SCC (or CTV) phenotype than cells from high $k_{io}$ samples.

Figure 17:
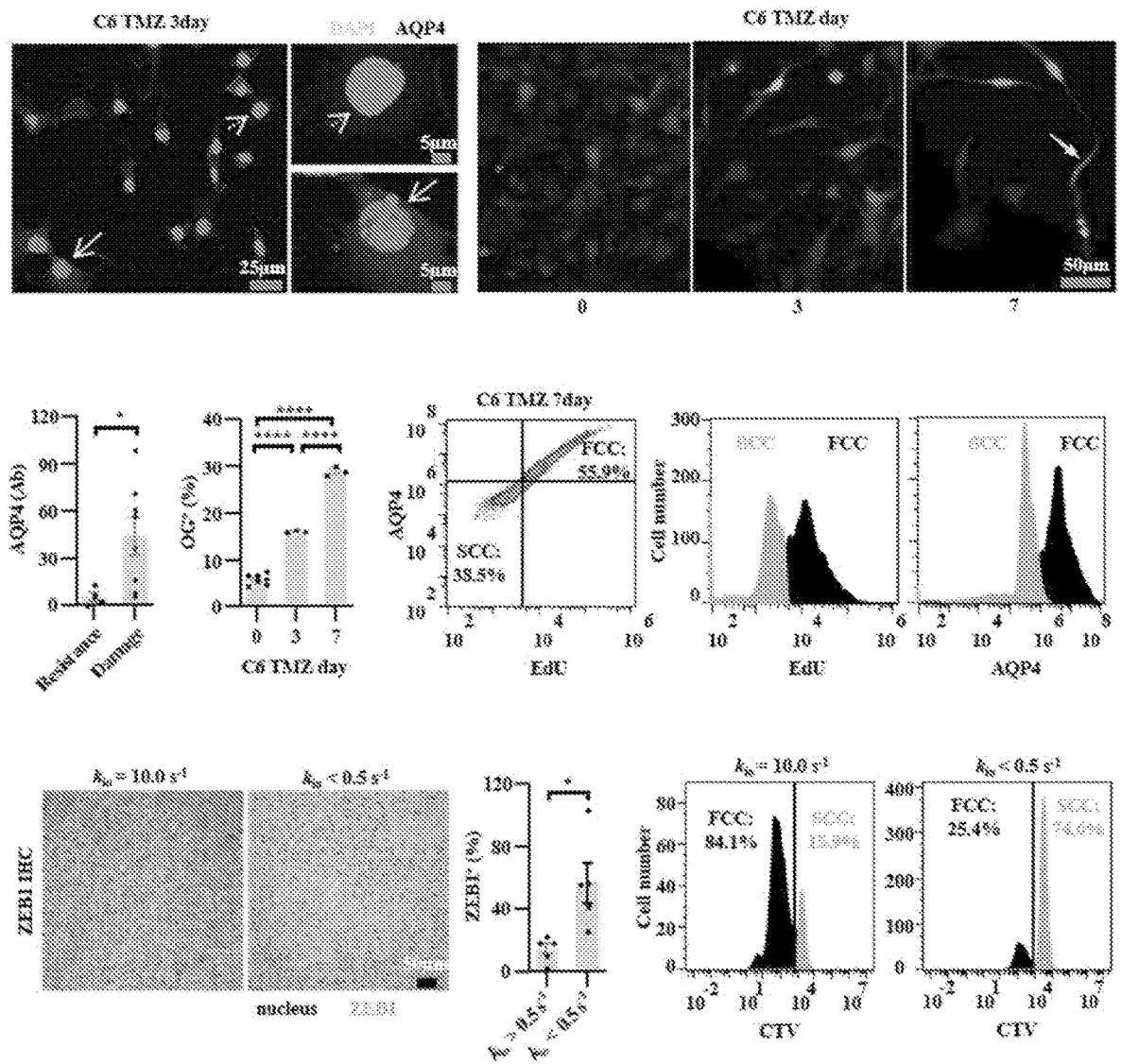
FIG. 17 shows that low $k_{io}$ (AQP4) reflects treatment-resistance glioma phenotypes.
Figure 18:
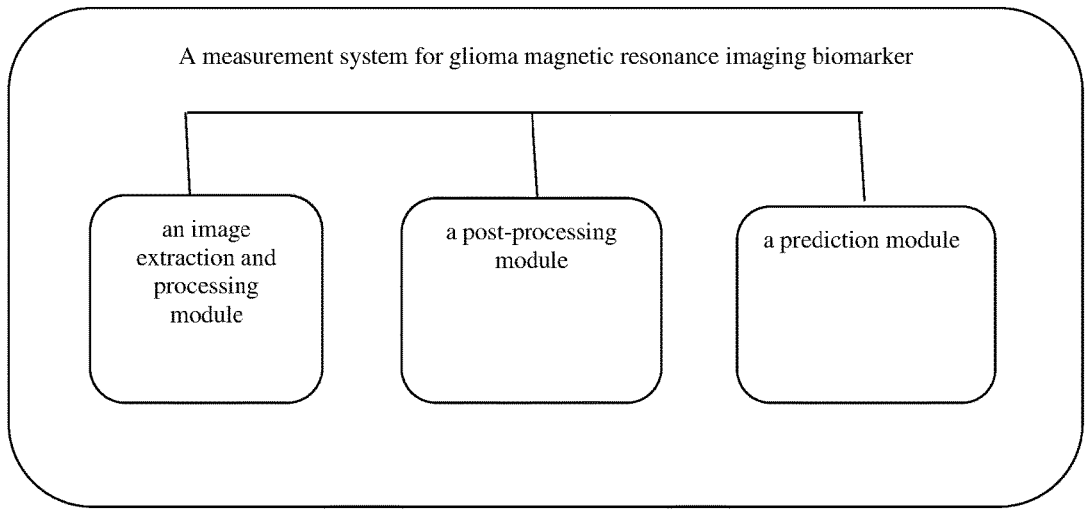
FIG. 18 shows an embodiment of a measurement system for glioma magnetic resonance imaging biomarker.
Figure 19:
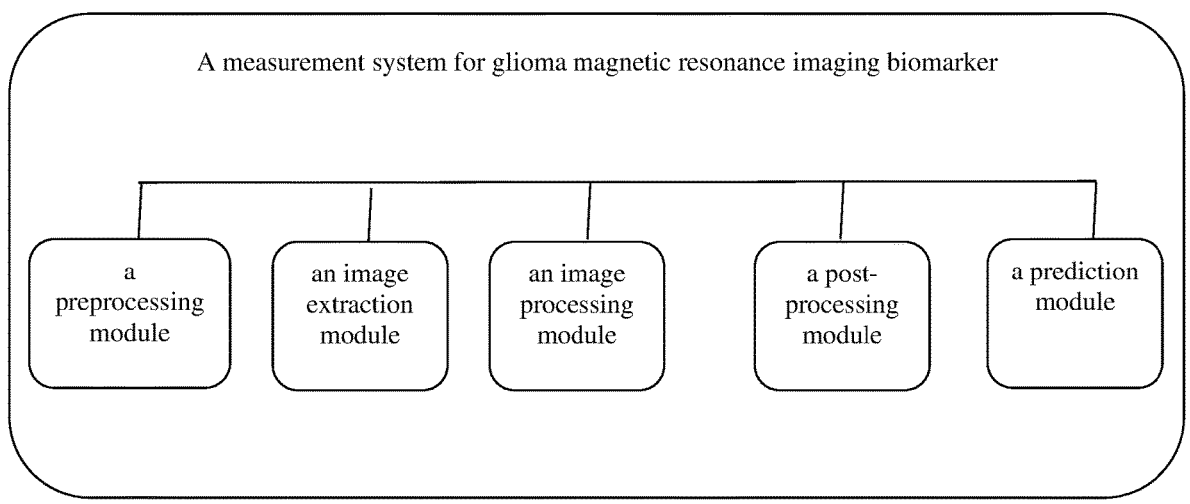
FIG. 19 shows another embodiment of a measurement system for glioma magnetic resonance imaging biomarker.

As shown in FIG. 17, low $k_{io}$ (AQP4) reflects the phenotype of treatment-resistant glioma: a: Confocal microscope images of AQP4 (red) and DAPI (blue) of C6 cells on the third day of TMZ treatment, some of which have nuclear damage (long-tailed arrow), while other cells show TMZ resistance, with more complete nuclear structure (short-tailed dotted arrow). The scale is 25 μM and 5 μM from left to right. b: Using OG-labeled cell tracing results, slow-circulating cells (SCC) showed high signal (long-tailed arrow) in the fluorogram. c: On the third day of treatment with TMZ, the quantitative results of AQP4 expression in the treatment-sensitive cells and treatment-resistant cells of C6 were obtained. The data is displayed as mean±standard error* $P<0.05$, here, p=0.0465, n=(4, 8). d: The bar graph shows that the proportion of SCC (OG+) increases after TMZ treatment, * * * $p<0.0001$, n=(7, 3, 3). e: The expression results of AQP4 and EdU on the 7th day of TMZ treatment were analyzed by flow cytometry. The two-dimensional scatter plot shows two different cell phenotypes, labeled FCC and SCC respectively. Glioma cells with slower proliferation (SCC, lower EdU) showed lower AQP4 expression (red) than fast-proliferating cells (FCC). f: ZEB1 results from stereotactic biopsy samples from patients with recurrent gliomas showed that the expression level of ZEB1 in low $k_{io}$ samples (right $k_{io}<0.5$ s$^{-1}$) was higher than that in high $k_{io}$ samples ($k_{io}>0.5$ s$^{-1}$). Scale: 50 Histogram statistics showed that compared with $k_{io}>0.5$ s$^{-1}$ (n=5), biopsy sites with $k_{io}<0.5$ s$^{-1}$ (n=5) showed more abundant ZEB1 expression (ZEB 1+score). The data of nucleus (blue) and ZEB1 (brown) are shown as mean±standard error * $p<0.05$, here, p=0.0260. In c, d, and f, the data points (such as the blue dot chart) cover the corresponding boxes, that is, the bilateral unpaired t-test. g: CTV flow sorting results of primary cells of clinical glioma biopsy samples obtained by stereotactic method, in which the proportion of SCC (CTV$^+$) shown from low $k_{io}$ samples (right) is much higher than that of primary cells obtained from high $k_{io}$ samples (left). In e and g, the black line indicates the gating selection of flow cytometer.

TMZ can inhibit the proliferation of glioma cells by inducing DNA double strand breaks, and kill the FCC subtype and retain the SCC subtype. TMZ treatment of C6 cell line revealed similar phenomena, including decreased proliferation and increased SCC score. In addition, the cell subtypes with low AQP4 expression level and long tail or pseudopodium morphology on the 7th day of TMZ are often considered as stem cell-like cells (GSCs) in GBM that are resistant to treatment. Similarly, the U87MG cell line also showed decreased proliferation and down-regulation of AQP4 during the quiescent and decaying stages of nutrition and oxygen deprivation. In these two microenvironments, $k_{io}$ obtained from water exchange DCE-MRI is closely related to the dynamic regulation of AQP4. In TMZ treatment (C6) and quiescent—proliferative reduction stage (U87MG), it was observed that the proportion of SCC with lower AQP4 expression level increased. This phenomenon is reasonable because SCC is a low proliferative cell subtype, and the expression level of AQP4 is related to cell proliferation. More importantly, low AQP4 expression can protect SCC from TMZ or other therapies by slowing down the transmembrane transport rate. In fact, C6 cell lines with low AQP4 expression were observed to have no or little nuclear damage under TMZ treatment, indicating their anti-TMZ status. In addition, low $k_{io}$ (i.e. low AQP4) biopsy samples from human glioma also showed higher expression of ZEB1, an anti-treatment biomarker, and a higher proportion of SCC. In general, these results show that $k_{io}$ is a potential method for SCC imaging and prediction of treatment response.

The spatial and temporal heterogeneity of AQP4 expression profile in glioma has great potential in promoting precise treatment and predicting treatment response. Since the expression of AQP4 is related to the degree of treatment resistance, the heterogeneity of $k_{io}$ may indicate the difference of treatment resistance in glioma region. This AQP4 expression profile has great potential in evaluating the pathological status of recurrent gliomas, and further affects the treatment strategy, resulting in many alternative methods for the treatment of recurrent gliomas. For example, if recurrent gliomas show high levels of $k_{io}$, the second radiotherapy and chemotherapy are preferred, because the high level of AQP4 expression indicates that tumor cells are sensitive to radiation and chemotherapy damage. Or, if low level of $k_{io}$ is measured, surgical intervention is preferred, because these tumor cells have strong resistance to radiotherapy or chemotherapy.

The present invention can accurately measure the heterogeneity of AQP4 within and between gliomas by using water exchange DCE-MRI to specifically and quantitatively measure the rate constant $k_{io}$ of intracellular transmembrane outflow, as an MRI biomarker sensitive to the expression level of AQP4. In previous studies, ADC from DWI also showed sensitivity to AQP4 silencing through RNA, but later results questioned this result. It is well known that water exchange may contribute to ADC, but the use of ADC in vivo lacks the specificity of transmembrane water exchange detection, and there are many possible biophysical mechanisms to induce ADC changes, including cell swelling or contraction, cell density and shape changes, and the shape of the gap, and there are more problems. Specifically, it has been proved that ADC mainly reflects the cell density in human glioma, which further hinders the use of ADC as a specific biomarker of water exchange in glioma.

In clinical practice, water-exchange DCE-MRI can be used together with conventional MRI scanning for glioma diagnosis by adding water-exchange DCE-MRI sequence during contrast agent (CA) injection without additional capital or time cost. In addition, conventional MRI can also be used to identify the tumor part of glioma from normal tissues or other tissues, so as to further analyze intratumoral AQP4 in water exchange DCE-MRI. The water-exchange DCE-MRI scanning scheme used in the invention can be further optimized to improve the accuracy of $k_{io}$ estimation and AQP4 detection, because individual differences can still be observed in rats (FIG. 12) and human glioma (f in FIG. 15). The areas to be improved include but are not limited to the optimization of MRI sequence, CA injection and SS model analysis.

Aquaporin 4 (AQP4) plays an important role in the fate of glioma, including tumor migration, proliferation and treatment resistance. Tissue biopsy can quantitatively characterize the expression level of AQP4 in vivo, but it cannot provide information about the heterogeneous distribution of AQP4 in the whole tumor. The invention provides a non-invasive magnetic resonance biomarker $k_{io}$ to detect and map AQP4 in glioma in vivo as a biomarker sensitive to the expression level of AQP4. AQP4 can be seen in MRI by quantitatively measuring the transmembrane water exchange regulated by AQP4. It is the first time to prove that AQP4 is the main way to regulate transmembrane water exchange, and $k_{io}$ is a sensitive biomarker of AQP4 expression in glioma. Then it demonstrated the precise detection ability of water-exchange DCE-MRI in various stages of glioma proliferation, temozolomide TMZ (clinical anticancer drug) treatment, gene knockout and TGN020 inhibition of AQP4 and other AQP4 expression and functional dynamic changes, and captured the spatial heterogeneity of AQP4 expression in rat glioma model and human glioma. In addition, low $k_{io}$ cells showed higher therapeutic resistance, indicating that AQP4 map has potential value in evaluating the therapeutic resistance of glioma. More importantly, this method can easily diagnose and evaluate glioma by radiology on the whole tumor MRI. This technology will significantly improve the accurate evaluation and treatment of human glioma.

The above specific implementation mode has described the technical scheme and beneficial effects of the invention in detail. It should be understood that the above is only the preferred embodiment of the invention and is not used to limit the invention. Any modification, supplement and equivalent replacement made within the scope of the principles of the invention should be included in the scope of protection of the invention.

The invention claimed is:

1. A measurement method of intracellular water transmembrane efflux rate ($k_{io}$), which is not for disease diagnosis, is used as a magnetic resonance imaging biomarker to evaluate the AQP4 expression level of glioma, where in, the measurement method is:
    (1) quantitatively measuring the intracellular water transmembrane efflux rate ($k_{io}$), by using dynamic-contrast-enhanced magnetic resonance imaging (DCE-MRI);
    (2) using a framed stereotactic biopsy technology to get biopsy tissue and quantitatively measuring its AQP4 expression level;
    (3) according to $k_{io}$ and AQP4 expression level, establishing a linear relationship between $k_{io}$ and AQP4; and
    (4) quantitatively re-measuring the intracellular water transmembrane efflux rate ($k_{io}$) of the tissue by using dynamic-contrast-enhanced magnetic resonance imaging (DCE-MRI), and the AQP4 expression level of the tissue is obtained according to the linear relationship in step (3).

2. The measurement method according to claim 1, wherein, the measurement method comprises the following steps:
    (a1) setting dynamic-contrast-enhanced magnetic resonance imaging (DCE-MRI) scanning parameters, and measuring a noise level of obtained DCE-MRI data;
    (a2) optimizing DCE-MRI scanning parameters by using monte Carlo simulation, and resetting a flip angle of DCE-MRI;
    (a3) scanning a quantitative T1 imaging;
    (a4) scanning a DCE-MRI and injecting the contrast agent;
    (a5) analyzing each voxel in the tumor region by using the Full Shutter-Speed model ($SSM_{full}$), and obtaining the intracellular water transmembrane efflux rate ($k_{io}$);
    (a6) according to the DCE-MRI, use the framed stereotactic biopsy technology to obtain biopsy tissue, and quantitatively measuring its AQP4 expression level;
    (a7) doing linear regression analysis of $k_{io}$ and AQP4 expression levels, and obtaining the linear equation between AQP4 expression level and $k_{io}$; and
    (a8) for the tissue, repeating steps (a3)-(a5), converting $k_{io}$ images into AQP4-expression-level imaging according to the linear equation in steps (a7) to obtain AQP4-expression-level imaging in tumor, wherein $k_{io}$ images are images composed of the $k_{io}$ value of each voxel in DCE-MRI calculated by the Full Shutter-Speed model ($SSM_{full}$) model, and the AQP4-expression-level imaging are composed of the AQP4 cell positivity rate of each voxel predicted by the linear equation between AQP4 expression level and kip.

3. The measurement method according to claim 2, wherein the details in step (a2) are as follows: one or more measured blood plasma contrast agent concentration $C_p$ are randomly selected, and then simulated DCE-MRI data at different flip angles is generated by using the parameters of human tissue and scanning parameters; the synthesized DCE-MRI time-series signal S(t) is generated by the $SSM_{full}$, and the white noise, whose noise level is the same as the noise level estimated from human DCE-MRI data, is added to S(t); then noise-added S(t) are fitted by the nonlinear least sum of square algorithm using the $SSM_{full}$; repeating the above steps and count the fitted $k_{io}$ for simulated DCE-MRI data at each flip angle; finally, the flip angle with the $k_{io}$ fitting result is closest to the simulated preset value and has the smallest variance is selected as the optimal flip angle;
    in step (a3), the quantitative T1 imaging is measured by multiple flip-angle and short repetition-time sequence.

4. The measurement method according to claim 2, wherein the details in step (a5) are as follows: using automatic shutter speed analysis method to obtain the vessel contrast agent transfer coefficient ($K^{trans}$) of each voxel in the tumor area, and only the voxels whose $K^{trans}$>0.01 min$^{-1}$ are further fitted by $SSM_{full}$ model to obtain the intracellular water transmembrane efflux rate ($k_{io}$).

5. The measurement method according to claim 2, wherein, a biopsy tissue AQP4 immunohistochemical image is obtained to quantify the tissue's AQP4 expression level in step (a6).

6. The measurement method according to claim 2, wherein, the linear relationship between intracellular water transmembrane efflux rate ($k_{io}$) and AQP4 expression level in step (a7) is: AQP4-positive fraction=($k_{io}$−A)/B,
    where the range of A is 0.1~0.2 s$^{-1}$ and the range of B is 13.07~15.04 s$^{-1}$.

7. The measurement method according to claim 2, wherein in evaluating AQP4 expression level, AQP4 expression level is evaluated through quantitative imaging of AQP4 expression.

8. The measurement method according to claim 7, wherein, the linear relationship between the intracellular water transmembrane efflux rate ($k_{io}$) and AQP4 expression level is: cellular AQP4-positive fraction=$(k_{io}-A)/B$,
where the range of A is 0.1~0.2 $s^{-1}$ and the range of B is 13.07~15.04 $s^{-1}$.

9. The measurement method according to claim 1, wherein the intracellular water transmembrane efflux rate is used as a magnetic resonance imaging biomarker of glioma to the application for making a product for predicting the sensitivity of glioma radiotherapy and chemotherapy.

10. The measurement method according to claim 9, wherein, the product used in the radiotherapy and chemotherapy treatment is Temozolomide.

11. A measurement system for glioma magnetic resonance imaging biomarker, wherein, the measurement system comprises:
an image extraction and processing module adapted for quantitatively measuring tissue's intracellular water transmembrane efflux rate ($ki_o$) by using dynamic-contrast-enhanced magnetic resonance imaging (DCE-MRI);
a post-processing module adapted for using a framed stereotactic biopsy technology to get biopsy tissue and quantitatively measuring its AQP4 expression level; and establishing a linear relationship between the $ki_o$ which is obtained from the image extraction and processing module and the AQP4 expression level of the biopsy tissue; and a prediction module adapted for re-measuring the $ki_o$ by using the image processing module, and using the linear relationship from post-processing module to predict the AQP4 expression level of tissue.

12. The measurement system for glioma magnetic resonance imaging biomarker according to claim 11, wherein the measurement system comprises:
a preprocessing module adapted for setting dynamic-contrast-enhanced magnetic resonance imaging (DCE-MRI) scanning parameters, and measuring the noise level of DCE-MRI data; through Monte Carlo simulation, optimizing the flip angle of DCE-MRI and resetting the optimized flip angle;

the image extraction module adapted for scanning quantitative T1 imaging, scanning DCE-MRI and injecting contrast agent;

the image processing module adapted for analyzing each voxel in tumor region by using the Full Shutter-Speed model ($SSM_{full}$), and obtaining the intracellular water transmembrane efflux rate of each voxel;

the post-processing module adapted for: establishing the linear relationship between the $k_{io}$ obtained by the image processing module and the AQP4 expression level of biopsy tissue; and the prediction module adapted for obtaining the $k_{io}$ by using the image extraction module and image processing module, and using the linear relationship from post-processing module to predict the AQP4 expression level of tissue.

* * * * *